(12) United States Patent
Chen et al.

(10) Patent No.: US 6,828,301 B2
(45) Date of Patent: Dec. 7, 2004

(54) PHARMACEUTICAL COMPOSITIONS FOR HEPATITIS C VIRAL PROTEASE INHIBITORS

(75) Inventors: Shirlynn Chen, Somers, NY (US); Xiaohui Mei, Highland Mills, NY (US)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 10/357,919

(22) Filed: Feb. 4, 2003

(65) Prior Publication Data

US 2003/0195228 A1 Oct. 16, 2003

Related U.S. Application Data

(60) Provisional application No. 60/355,694, filed on Feb. 7, 2002.

(51) Int. Cl.[7] ........................ A61K 47/18; A61K 38/05
(52) U.S. Cl. ............... 514/9; 514/10; 514/11; 514/18; 514/19
(58) Field of Search .................. 514/9, 10, 11, 514/18, 19

(56) References Cited

U.S. PATENT DOCUMENTS

| 4,388,307 | A | 6/1983 | Cavanak |
|---|---|---|---|
| 5,071,643 | A | 12/1991 | Yu et al. |
| 5,342,625 | A | 8/1994 | Hauer et al. |
| 5,360,615 | A | 11/1994 | Yu et al. |
| 5,376,688 | A | 12/1994 | Morton et al. |
| 5,504,068 | A | 4/1996 | Komiya et al. |
| 6,056,977 | A | 5/2000 | Bhagwat et al. |
| 6,121,313 | A | 9/2000 | Gao et al. |
| 6,231,887 | B1 | 5/2001 | Gao et al. |

FOREIGN PATENT DOCUMENTS

| WO | WO 93/20833 | 10/1993 |
|---|---|---|
| WO | WO 96/36316 | 11/1996 |
| WO | WO 99/06044 A1 | 2/1999 |
| WO | WO 00/59929 A1 | 10/2000 |

OTHER PUBLICATIONS

Tsantrizos, et al, "Macrocyclic Peptides Active Against The hepatitis C Virus"; USSN 09/760,946; filed Jan. 16, 2001.

Primary Examiner—Bruck Kifle
(74) Attorney, Agent, or Firm—Robert Raymond; Michael Morris; Philip I. Datlow

(57) ABSTRACT

Disclosed are pharmaceutical compositions of hepatitis C viral protease inhibitors having improved bioavailability, and methods of using these compositions for inhibiting the replication of the hepatitis C virus (HCV) and for the treatment of an HCV infection. These compositions include co-solvent systems, lipid based systems, solid dispersions and granulations, and all comprise the hepatitis C viral protease inhibitor, at least one pharmaceutically acceptable amine and optionally one or more additional ingredients.

77 Claims, 2 Drawing Sheets

PHARMACEUTICAL COMPOSITIONS FOR HEPATITIS C VIRAL PROTEASE INHIBITORS

RELATED APPLICATIONS

This application claims the benefit of U.S. Provisional Application No. 60/355,694, filed Feb. 7, 2002, which is herein incorporated by reference in its entirety.

FIELD OF THE INVENTION

The present invention relates in general to pharmaceutical compositions of hepatitis C viral protease inhibitors having improved bioavailability, and methods of using these compositions for inhibiting the replication of the hepatitis C virus (HCV) and for the treatment of an HCV infection.

BACKGROUND OF THE INVENTION

It has recently been discovered that certain macrocyclic compounds are potent and specific inhibitors of hepatitis C virus (HCV) protease. In particular, compounds of the following formula I have been found to be an especially potent class of inhibitors against the NS3 serine protease of HCV:

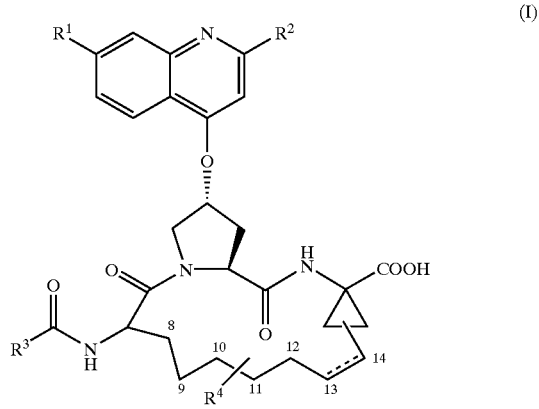

(I)

wherein:
- —— designates an optional bond forming a double bond between positions 13 and 14;
- $R^1$ is H, halo, $C_{1-6}$ alkyl, $C_{3-6}$ cycloalkyl, $C_{1-6}$ haloalkyl, $C_{1-6}$ alkoxy, $C_{3-6}$ cycloalkoxy, hydroxy, or $N(R^5)_2$, wherein each $R^5$ is independently H, $C_{1-6}$ alkyl or $C_{3-6}$ cycloalkyl;
- $R^2$ is H, halo, $C_{1-6}$ alkyl, $C_{3-6}$ cycloalkyl, $C_{1-6}$ haloalkyl, $C_{1-6}$ thioalkyl, $C_{1-6}$ alkoxy, $C_{3-6}$ cycloalkoxy, $C_{2-7}$ alkoxyalkyl, $C_{6\,or\,10}$ aryl or Het, wherein Het is a five-, six-, or seven-membered saturated or unsaturated heterocycle containing from one to four ring heteroatoms selected from nitrogen, oxygen and sulfur;
said cycloalkyl, aryl or Het being optionally substituted with $R^6$, wherein $R^6$ is H, halo, $C_{1-6}$ alkyl, $C_{3-6}$ cycloalkyl, $C_{1-6}$ alkoxy, $C_{3-6}$ cycloalkoxy, $NO_2$, $N(R^7)_2$, NH—C(O)—$R^7$; or NH—C(O)—NH—$R^7$, wherein each $R^7$ is independently: H, $C_{1-6}$ alkyl or $C_{3-6}$ cycloalkyl;
or $R^6$ is NH—C(O)—$OR^8$ wherein $R^8$ is $C_{1-6}$ alkyl or $C_{3-6}$ cycloalkyl;
- $R^3$ is $R^9$O— or $R^9$NH—, wherein $R^9$ is $C_{1-6}$alkyl or $C_{3-6}$cycloalkyl;
- $R^4$ is H or from one to three substituents on any available carbon atom at positions 8, 9, 10, 11, 12, 13 or 14, said substituent independently selected from the group consisting of: $C_{1-6}$ alkyl, $C_{1-6}$ haloalkyl, $C_{1-6}$ alkoxy, hydroxy, halo, amino, oxo, thio or $C_{1-6}$ thioalkyl;

See Tsantrizos et al., U.S. application Ser. No. 09/760,946, filed on Jan. 16, 2001, (Boehringer Ingelheim (Canada), Ltd.), which application is herein incorporated by reference in its entirety and is hereinafter referred to as "Tsantrizos et al". See also the corresponding WO 00/59929 (Boehringer Ingelheim (Canada) Ltd.).

A structural feature of the compounds of formula I is the presence of the C-terminal carboxylic acid functionality, which was shown to be responsible not only for the potency and reversibility observed for this inhibitor series, but also for the excellent specificity for HCV protease compared to other serine/cysteine proteases. An HCV serine protease inhibitor such as the compounds of formula I would be expected to be an antiviral agent acting via a novel mechanism, i.e. blockage of a virus-encoded essential function for HCV replication. A drug acting through this mechanism should suppress viral replication of all HCV genotypes and therefore provide tangible benefits to patients with chronic hepatitis C.

A common problem among protease inhibitors is that these compounds are lipophilic and have low aqueous solubility. Because of the poor aqueous solubility, conventional solid and liquid pharmaceutical preparations containing these inhibitors may not be absorbed by the patient in a satisfactory manner. Of the various factors that can affect the bioavailability of a drug when administered orally, (which include aqueous solubility, drug absorption through the gastrointestinal tract, dosage strength and first pass effect), aqueous solubility is often found to be among the most important factors. Poorly water soluble compounds often exhibit either erratic or incomplete absorption in the digestive tract, and thus produce a less than desirable response.

The compounds of formula I are zwitterionic and are capable of forming salts with strong acids and bases. Attempts to identify salts of such compounds in solid forms, which would substantially improve aqueous solubility, have not been successful. Various salts of these compounds have been found to be very hygroscopic, reducing the stability of the compounds. In addition, formulations of salts of these compounds generally are prone to precipitation of the parent free-acid in the gastrointestinal tract. Representative compounds of formula I have shown poor bioavailability when administered to animals as an aqueous suspension, suggesting that conventional formulations containing these inhibitors may not be absorbed in a satisfactory manner. Thus, there is a need in the art for pharmaceutical compositions of the formula I compounds having improved bioavailability.

Methods of formulating certain lipophilic macrocyclic compounds into pharmaceutical formulations have been previously reported. For example, Cavanak, U.S. Pat. No. 4,388,307, discloses the preparation of emulsified formulations of commercially available cyclosporins, and Hauer et. al, U.S. Pat. No. 5,342,625, and Meizner et al. WO 93/20833 disclose the preparation of cyclosporin microemulsions and microemulsion pre-concentrates. Komiya et. al, U.S. Pat. No. 5,504,068, further discloses the preparation of an enhanced topical formulations of cyclosporin.

Examples of "self-emulsifying" formulations of lipophilic compounds include Lipari et al, WO 96/36316, which discloses a self-emulsifying pre-concentrate comprising a lipophilic compound, d-alpha-tocopheryl polyethylene glycol 1000 succinate (TPGS) and a lipophilic phase. Gao et al., U.S. Pat. No. 6,121,313 discloses a self-emulsifying formulation of a pyranone protease inhibitor comprising the pyranone compound, a mixture of mono- and di-glycerides, one or more solvents and one or more surfactants; and Gao et al, U.S. Pat. No. 6,231,887 B1 discloses a self-emulsifying formulation of a pyranone protease inhibitor comprising the pyranone compound, an amine, one or more solvents and one or more surfactants.

Yu et. al U.S. Pat. Nos. 5,360,615 and 5,071,643 disclose the preparation of a solvent system for enhancing the solubility of acidic, basic or amphoteric compounds by partial ionization comprising a mixture of polyethylene glycol, hydroxide or hydrogen ion, and water. Morton et al U.S. Pat. No. 5,376,688 discloses solutions of acidic, basic or amphoteric pharmaceutical agents comprising the pharmaceutical agent, an ionic species and a solvent system. Bhagwat et. al U.S. Pat. No. 6,056,977 teaches the use of polysaccharide based matrix for sustained release of a sulfonylurea.

Despite these advances, there continues to be a need in the art for oral pharmaceutical compositions of the zwitterionic compounds of formula I having improved bioavailability.

BRIEF SUMMARY OF THE INVENTION

The present invention overcomes the aforementioned problems by providing pharmaceutical compositions of the formula I compounds having improved bioavailability as compared to conventional pharmaceutical formulations. In particular, specific compositions of the present invention have demonstrated excellent in vitro dissolution profiles and have achieved marked increases in bioavailability as compared to conventional pharmaceutical formulations.

The pharmaceutical compositions of the present invention cover a wide variety of types of compositions, but all comprise a compound of formula I together with one or more pharmaceutically acceptable amines. The compositions of the present invention may include one or more additional ingredients depending on the type of composition contemplated, e.g., pharmaceutically acceptable solvents, surfactants, oils, polymers, etc., as will be discussed in more detail below. The present invention is also directed to the methods of manufacturing these compositions, as described hereinafter.

In a general embodiment, the pharmaceutical composition of the present invention comprises:

(a) a compound of formula (I):

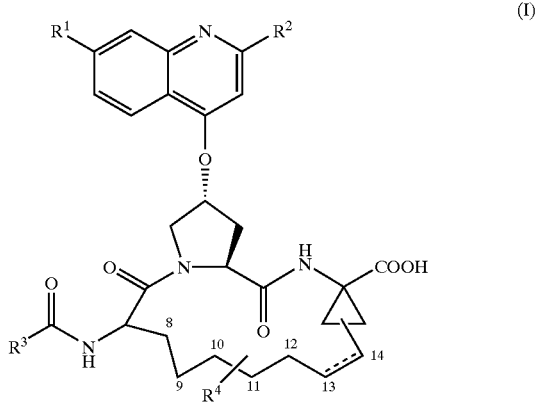

wherein:
——— designates an optional bond forming a double bond between positions 13 and 14;

$R^1$ is H, halo, $C_{1-6}$ alkyl, $C_{3-6}$ cycloalkyl, $C_{1-6}$ haloalkyl, $C_{1-6}$ alkoxy, $C_{3-6}$ cycloalkoxy, hydroxy, or $N(R^5)_2$, wherein each $R^5$ is independently H, $C_{1-6}$ alkyl or $C_{3-6}$ cycloalkyl;

$R^2$ is H, halo, $C_{1-6}$ alkyl, $C_{3-6}$ cycloalkyl, $C_{1-6}$ haloalkyl, $C_{1-6}$ thioalkyl, $C_{1-6}$ alkoxy, $C_{3-6}$ cycloalkoxy, $C_{2-7}$ alkoxyalkyl, $C_{6\ or\ 10}$ aryl or Het, wherein Het is a five-, six-, or seven-membered saturated or unsaturated heterocycle containing from one to four ring heteroatoms selected from nitrogen, oxygen and sulfur;

said cycloalkyl, aryl or Het being optionally substituted with $R^6$, wherein $R^6$ is H, halo, $C_{1-6}$ alkyl, $C_{3-6}$ cycloalkyl, $C_{1-6}$ alkoxy, $C_{3-6}$ cycloalkoxy, $NO_2$, $N(R^7)_2$, NH—C(O)—$R^7$; or NH—C(O)—NH—$R^7$, wherein each $R^7$ is independently: H, $C_{1-6}$ alkyl or $C_{3-6}$ cycloalkyl;

or $R^6$ is NH—C(O)—$OR^8$ wherein $R^8$ is $C_{1-6}$ alkyl or $C_{3-6}$ cycloalkyl;

$R^3$ is $R^9O$— or $R^9NH$—, wherein $R^9$ is $C_{1-6}$alkyl or $C_{3-6}$cycloalkyl;

$R^4$ is H or from one to three substituents on any available carbon atom at positions 8, 9, 10, 11, 12, 13 or 14, said substituent independently selected from the group consisting of: $C_{1-6}$ alkyl, $C_{1-6}$ haloalkyl, $C_{1-6}$ alkoxy, hydroxy, halo, amino, oxo, thio or $C_{1-6}$ thioalkyl; or a tautomer thereof;

(b) about 0.1 to 10% by weight of a pharmaceutically acceptable amine or a mixture of pharmaceutically acceptable amines; and (c) one or more pharmaceutically acceptable oils, carriers or hydrophilic solvents;

and when (c) is one or more pharmaceutically acceptable oils, the pharmaceutical composition further comprises:

(d) optionally one or more pharmaceutically acceptable hydrophilic solvents;

(e) optionally one or more pharmaceutically acceptable polymers; and (f) optionally one or more pharmaceutically acceptable surfactants;

and when (c) is one or more pharmaceutically acceptable carriers, the pharmaceutical composition further comprises:

(d) optionally one or more pharmaceutically acceptable surfactants.

Another important aspect of the present invention involves a method of inhibiting the replication of hepatitis C virus by exposing the virus to a hepatitis C viral NS3 protease-inhibiting amount of a pharmaceutical composition of the present invention.

Another important aspect of the present invention involves a method of treating a hepatitis C viral infection in a mammal by administering to the mammal in need thereof a therapeutically effective amount of a pharmaceutical composition of the present invention.

DETAILED DESCRIPTION OF THE INVENTION

Definition of Terms and Conventions Used

Figure 1:
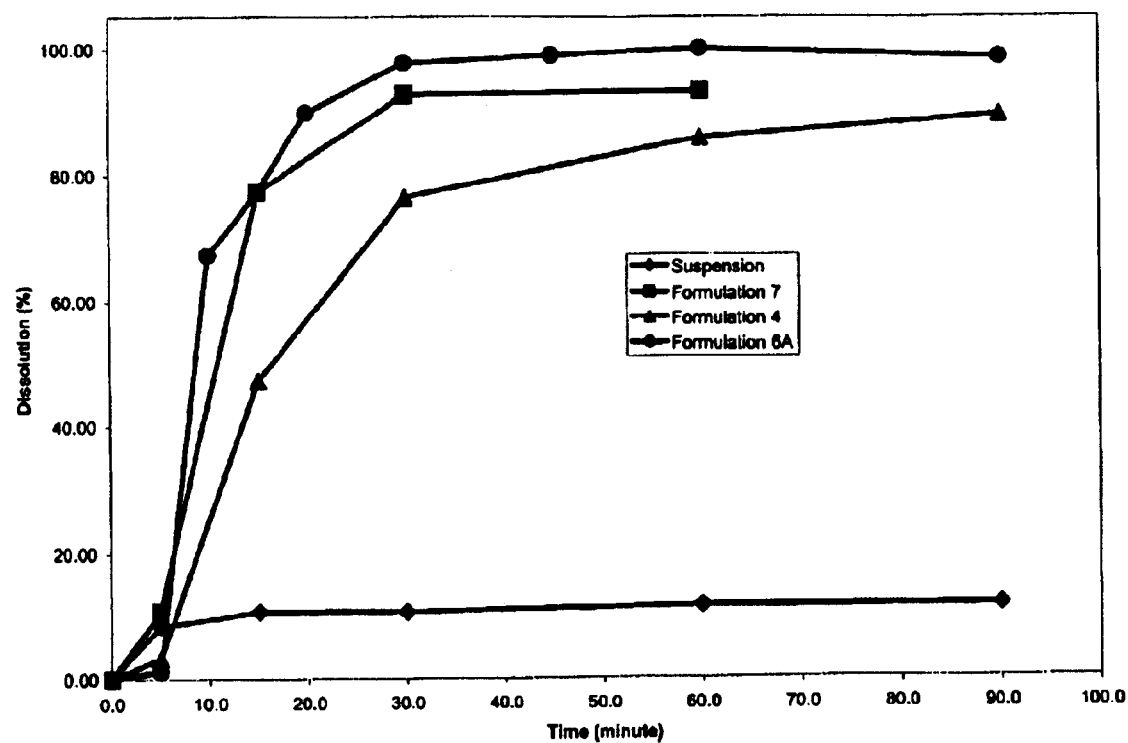
FIG. 1 shows the in-vitro dissolution profiles of three formulations according to the present invention containing tromethamine (SEDDS and solid dispersion) and a comparative formulation without tromethamine (1% CMC/0.2% Tween 80).

Terms not specifically defined herein should be given the meanings that would be given to them by one of skill in the art in light of the disclosure and the context. As used in the specification, however, unless specified to the contrary, the following terms have the meaning indicated and the following conventions are adhered to.

A. Chemical and Pharmaceutical Nomenclature, Terms, and Conventions

In the groups, radicals, or moieties defined below, the number of carbon atoms is often specified preceding the group, for example, $C_{1-6}$ alkyl means an alkyl group or radical having 1 to 6 carbon atoms. In general, for groups comprising two or more subgroups, the last named group is the radical attachment point, for example, "thioalkyl" means a monovalent radical of the formula HS—Alk—. Unless otherwise specified below, conventional definitions of terms control and conventional stable atom valences are presumed and achieved in all formulas and groups. The term "$C_{1-6}$ alkyl" as used herein, either alone or in combination with another substituent, means acyclic, straight or branched chain alkyl substituents containing from 1 to six carbon atoms and includes, for example, methyl, ethyl, propyl, butyl, hexyl, 1-methylethyl, 1-methylpropyl, 2-methylpropyl, and 1,1-dimethylethyl.

The term "$C_{3-6}$ cycloalkyl" as used herein, either alone or in combination with another substituent, means a cycloalkyl substituent containing from three to six carbon atoms and includes cyclopropyl, cyclobutyl, cyclopentyl, and cyclohexyl.

The term "$C_{1-6}$ alkoxy" as used herein, either alone or in combination with another substituent, means the substituent $C_{1-6}$ alkyl-O— wherein alkyl is as defined above containing up to six carbon atoms. Alkoxy includes methoxy, ethoxy, propoxy, 1-methylethoxy, butoxy and 1,1-dimethylethoxy. The latter substituent is known commonly as tert-butoxy.

The term "$C_{3-6}$ cycloalkoxy" as used herein, either alone or in combination with another substituent, means the substituent $C_{3-6}$ cycloalkyl-O— containing from 3 to 6 carbon atoms.

The term "halo" as used herein means a halogen substituent selected from bromo, chloro, fluoro or iodo.

The term "haloalkyl" as used herein means as used herein, either alone or in combination with another substituent, means acyclic, straight or branched chain alkyl substituents having one or more hydrogens substituted for a halogen selected from bromo, chloro, fluoro or iodo.

The term "thioalkyl" as used herein means as used herein, either alone or in combination with another substituent, means acyclic, straight or branched chain alkyl substituents containing a thiol (HS) group as a substituent. An example of a thioalkyl group is a thiopropyl, e.g., HS—CH$_2$CH$_2$CH$_2$— is one example of a thiopropyl group.

The term "$C_6$ or $C_{10}$ aryl" as used herein, either alone or in combination with another substituent, means either an aromatic monocyclic system containing 6 carbon atoms or an aromatic bicyclic system containing 10 carbon atoms. For example, aryl includes a phenyl or a naphthyl—ring system.

The term "Het" as used herein, either alone or in combination with another substituent, means a monovalent substituent derived by removal of a hydrogen from a five-, six-, or seven-membered saturated or unsaturated (including aromatic) heterocycle containing carbon atoms and from one to four ring heteroatoms selected from nitrogen, oxygen and sulfur. Examples of suitable heterocycles include: tetrahydrofuran, thiophene, diazepine, isoxazole, piperidine, dioxane, morpholine, pyrimidine or

The term "Het" also includes a heterocycle as defined above fused to one or more other cycle be it a heterocycle or any other cycle. One such examples includes thiazolo[4,5-b]-pyridine. Although generally covered under the term "Het", the term "heteroaryl" as used herein precisely defines an unsaturated heterocycle for which the double bonds form an aromatic system. Suitable example of heteroaromatic system include: quinoline, indole, pyridine,

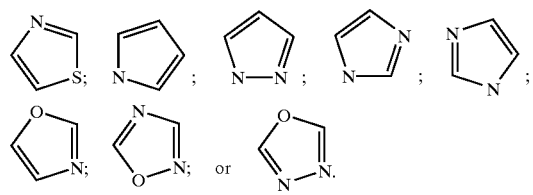

The term "oxo" means the double-bonded group (═O) attached as a substituent.

The term "thio" means the double-bonded group (═S) attached as a substituent.

The term "compounds of the invention", and equivalent expressions, are meant to embrace compounds of Formula (I) as herein described, including the tautomers and isomers thereof, where the context so permits. In general, the compounds of the invention and the formulas designating the compounds of the invention are understood to only include the stable compounds thereof and exclude unstable compounds, even if an unstable compound might be considered to be literally embraced by the compound formula.

The term "stable compound" means a compound that is sufficiently robust to survive isolation to a useful degree of purity from a reaction mixture and formulation into an efficacious pharmaceutical composition. For example, a compound which would have a "dangling valency" or is a "carbanion" is not a compound contemplated by the invention.

The term "pharmaceutical composition of the invention" and equivalent expressions is meant to embrace all the various types of pharmaceutical compositions as described hereinafter, unless it is clear from the context that reference is being made to a particular type of pharmaceutical composition within the scope of the present invention.

The term "pharmaceutically acceptable" with respect to a substance as used herein means that substance which is, within the scope of sound medical judgment, suitable for use in contact with the tissues of humans and lower animals without undue toxicity, irritation, allergic response, and the like, commensurate with a reasonable benefit/risk ratio, and effective for the intended use when the substance is used in a pharmaceutical composition.

The term "semi-solid" means a material that is neither solid (elastic behavior) nor liquid (viscous behavior) and possesses the characteristics of both viscosity and elasticity. Examples of semi-solid materials include gels, ointments, creams, and highly viscous liquids.

The term "about" means within 20%, preferably within 10%, and more preferably within 5% of a given value or range. For example, "about 10%" means from 8% to 12%, preferably from 9% to 11%, and more preferably from 9.5% to 10.5%. When the term "about" is associated with a range of values, e.g., "about X to Y %", the term "about" is intended to modify both the lower (X) and upper (Y) values of the recited range. For example, "about 0.1 to 10%" is equivalent to "about 0.1% to about 10%".

All percentages recited for amounts of ingredients in the compositions are percentages by weight with respect to the whole composition.

B. Isomer Terms and Conventions

The terms "isomers" or "stereoisomers" mean compounds having the same number and kind of atoms, and hence the same molecular weight, but differing in respect to the arrangement or configuration of the atoms in space. The term includes optical isomers and geometric isomers.

The term "optical isomer" means a stable isomer that has at least one chiral atom or restricted rotation giving rise to perpendicular dissymmetric planes (e.g., certain biphenyls, allenes, and spiro compounds) and can rotate plane-polarized light. Because asymmetric centers and other chemical structure exist in the compounds of formula I which may give rise to optical isomerism, the invention contemplates optical isomers and mixtures thereof. The compounds of formula I include asymmetric carbon atoms and may therefore exist as single stereoisomers, racemates, and as mixtures of enantiomers and diastereomers. Typically, such compounds will be prepared as a racemic mixture. If desired, however, such compounds can be prepared or isolated as pure optical isomers, i.e., as individual enantiomers or diastereomers, or as stereoisomer-enriched mixtures. Individual stereoisomers of compounds are prepared by synthesis from optically active starting materials containing the desired chiral centers or by preparation of mixtures of enantiomeric products followed by separation, such as conversion to a mixture of diastereomers followed by separation or recrystallization, chromatographic techniques, use of chiral resolving agents, or direct separation of the enantiomers on chiral chromatographic columns. Starting compounds of particular stereochemistry are either commercially available or are made by the methods described below and resolved by techniques well-known in the art.

The term "enantiomers" means a pair of optical isomers that are non-superimposable mirror images of each other.

The term "diastereoisomers" means optical isomers which are not mirror images of each other.

The term "racemic mixture" means a mixture containing equal parts of individual enantiomers.

The term "non-racemic mixture" means a mixture containing unequal parts of individual enantiomers or stereoisomers.

The term "geometrical isomer" means a stable isomer which results from restricted freedom of rotation about double bonds (e.g., cis-2-butene and trans-2-butene) or in a cyclic structure (e.g., cis-1,3-dichlorocyclobutane and trans-1,3-dichlorocyclobutane). Because carbon-carbon double (olefinic) bonds, cyclic structures, and the like may be present in the compounds of formula I, the invention contemplates each of the various stable geometric isomers and mixtures thereof resulting from the arrangement of substituents around these double bonds and in these cyclic structures. The substituents and the isomers are designated using the cis/trans convention.

Some of the compounds of formula I can exist in more than one tautomeric form. As mentioned above, the compounds of formula I include all such tautomers.

In general, all tautomeric forms and isomeric forms and mixtures thereof, for example, individual geometric isomers, stereoisomers, optical isomers or racemic or non-racemic mixtures of isomers, of a chemical structure or compound is intended, unless the specific stereochemistry or isomeric form is specifically indicated in the compound name or structure.

C. Pharmaceutical Administration and Treatment Terms and Conventions

The term "patient" includes both human and non-human mammals.

The term "therapeutically effective amount" means an amount of a compound according to the invention which, when administered to a patient in need thereof, is sufficient to effect treatment of a hepatitis C viral infection. Such a therapeutically effective amount can be determined routinely by one of ordinary skill in the art having regard to their own knowledge, the prior art, and this disclosure.

The terms "treating" or "treatment" mean the treatment of a hepatitis C viral infection in a patient, and include:
(i) preventing the hepatitis C viral infection from occurring in a patient, in particular, when such patient is predisposed to such disease-state but has not yet been diagnosed as having it;
(ii) inhibiting or ameliorating the hepatitis C viral infection, i.e., arresting or slowing its development; or
(iii) relieving the hepatitis C viral infection, i.e., causing regression or cure of the disease-state.

Preferred Embodiments of the Invention

1. Co-Solvent System

A first embodiment which we refer to herein as the "co-solvent" system is directed to a pharmaceutical composition comprising:
(a) a compound of formula (I):

wherein:

---- designates an optional bond forming a double bond between positions 13 and 14;

$R^1$ is H, halo, $C_{1-6}$ alkyl, $C_{3-6}$ cycloalkyl, $C_{1-6}$ haloalkyl, $C_{1-6}$ alkoxy, $C_{3-6}$ cycloalkoxy, hydroxy, or $N(R^5)_2$, wherein each $R^5$ is independently H, $C_{1-6}$ alkyl or $C_{3-6}$ cycloalkyl;

$R^2$ is H, halo, $C_{1-6}$ alkyl, $C_{3-6}$ cycloalkyl, $C_{1-6}$ haloalkyl, $C_{1-6}$ thioalkyl, $C_{1-6}$ alkoxy, $C_{3-6}$ cycloalkoxy, $C_{2-7}$ alkoxyalkyl, $C_{6\ or\ 10}$ aryl or Het, wherein Het is a five-, six-, or seven-membered saturated or unsaturated heterocycle containing from one to four ring heteroatoms selected from nitrogen, oxygen and sulfur;

said cycloalkyl, aryl or Het being optionally substituted with $R^6$, wherein $R^6$ is H, halo, $C_{1-6}$ alkyl, $C_{3-6}$ cycloalkyl, $C_{1-6}$ alkoxy, $C_{3-6}$ cycloalkoxy, $NO_2$, $N(R^7)_2$, NH—C(O)—

R[7]; or NH—C(O)—NH—R[7], wherein each R[7] is independently: H, $C_{1-6}$ alkyl or $C_{3-6}$ cycloalkyl;

or R[6] is NH—C(O)—OR[8] wherein R[8] is $C_{1-6}$ alkyl or $C_{3-6}$ cycloalkyl;

R[3] is R[9]O— or R[9]NH—, wherein R[9] is $C_{1-6}$alkyl or $C_{3-6}$cycloalkyl;

R[4] is H or from one to three substituents on any available carbon atom at positions 8, 9, 10, 11, 12, 13 or 14, said substituent independently selected from the group consisting of: $C_{1-6}$ alkyl, $C_{1-6}$ haloalkyl, $C_{1-6}$ alkoxy, hydroxy, halo, amino, oxo, thio or $C_{1-6}$ thioalkyl;

or a tautomer thereof;

(b) about 0.1 to 10% by weight of a pharmaceutically acceptable amine or a mixture of pharmaceutically acceptable amines; and (c) one or more pharmaceutically acceptable hydrophilic solvents.

The amount of the active ingredient (formula (I) compound) that may be present in the co-solvent system composition may vary widely or be adjusted widely depending on the intended route of administration, the potency of the particular active ingredient being used, the severity of the hepatitis C viral infection and the required concentration. In a particular embodiment, the compound of formula (I) is present in the co-solvent system composition in an amount of from about 1% to 50% by weight, preferably from about 5% to 30% by weight, more preferably from about 5% to 15% by weight.

Pharmaceutically acceptable amines useful in the composition include, for example, $C_{1-6}$ alkylamine, di-($C_{1-6}$ alkyl)-amine or tri-($C_{1-6}$ alkyl)-amine, wherein one or more alkyl groups thereof may be optionally substituted by one or more hydroxy groups, or $C_{1-6}$ alkylenediamine, a basic amino acid or choline hydroxide, or mixtures thereof. Specific amines include ethanolamine, diethanolamine, triethanolamine, tris(hydroxymethyl)aminomethane, ethylenediamine or dimethylaminoethanol, or mixtures thereof. A preferred amine is tris(hydroxymethyl)aminomethane (also called "Tris" or "Tromethamine"). The amine is present in an amount of about 0.1 to 10% by weight, more preferably in an amount of from about 0.5% to 7% by weight; even more preferably from about 0.5% to 5% by weight.

Pharmaceutically acceptable hydrophilic solvents useful in the composition include, for example, propylene glycol, polypropylene glycol, polyethylene glycol (e.g. PEG 400), glycerol, ethanol, dimethyl isosorbide, glycofurol, propylene carbonate, dimethyl acetamide, water, or mixtures thereof; preferably, propylene glycol, polyethylene glycol, ethanol, water, or mixtures thereof. A preferred solvent is a mixture of propylene glycol, ethanol and water. The amount of solvent(s) in the composition may vary over a wide range and the optimum amount for a particular composition will depend on the type and amount of other ingredients in the composition as can be easily determined by the skilled worker. In general, however, the solvent(s) are present in an amount of from about 40% to 99% by weight, preferably from about 80% to 99% by weight, more preferably, from about 80% to 90% by weight.

A particular embodiment of the co-solvent system is directed to a pharmaceutical composition, comprising:

(a) about 5% to 30% by weight of a compound of formula (I);

(b) about 0.5% to 7% by weight of a pharmaceutically acceptable amine; and (c) about 40% to 99% by weight of pharmaceutically acceptable hydrophilic solvent.

A further particular embodiment of the co-solvent system is directed to a pharmaceutical composition, comprising:

(a) about 5% to 15% by weight of a compound of formula (I);

(b) about 0.5% to 5% by weight of a pharmaceutically acceptable amine; and (c) about 80% to 99% by weight of pharmaceutically acceptable hydrophilic solvent.

A further particular embodiment of the co-solvent system is directed to a pharmaceutical composition, comprising:

(a) about 5% to 15% by weight of a compound of formula (I);

(b) about 0.5% to 5% by weight of tris(hydroxymethyl) aminomethane; and (c) about 80% to 90% by weight of a mixture of propylene glycol, ethanol and water.

The co-solvent system composition may be prepared in a conventional manner, for example, by dissolving the amine (s) in the pharmaceutically acceptable solvent(s), adding the compound of formula (I) to the resulting solution and then mixing the resulting solution until all or substantially all of the compound of formula I is solubilized in the solution. This method of preparing the composition constitutes another aspect of the present invention. The resulting solution is then formulated into the desired dosage form such as topical, parenteral and in particular oral dosage forms.

II. Lipid-Based System

A second embodiment which we refer to herein as the "Lipid-Based System" is directed to a pharmaceutical composition comprising:

(a) a compound of formula (I):

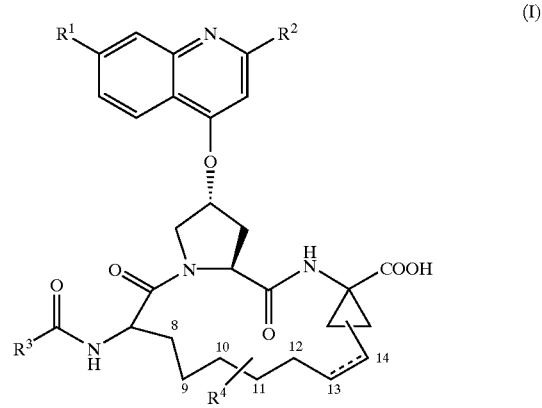

wherein:

---- designates an optional bond forming a double bond between positions 13 and 14;

R[1] is H, halo, $C_{1-6}$ alkyl, $C_{3-6}$ cycloalkyl, $C_{1-6}$ haloalkyl, $C_{1-6}$ alkoxy, $C_{3-6}$ cycloalkoxy, hydroxy, or $N(R^5)_2$, wherein each R[5] is independently H, $C_{1-6}$ alkyl or $C_{3-6}$ cycloalkyl;

R[2] is H, halo, $C_{1-6}$ alkyl, $C_{3-6}$ cycloalkyl, $C_{1-6}$ haloalkyl, $C_{1-6}$ thioalkyl, $C_{1-6}$ alkoxy, $C_{3-6}$ cycloalkoxy, $C_{2-7}$ alkoxyalkyl, $C_{6\,or\,10}$ aryl or Het, wherein Het is a five-, six-, or seven-membered saturated or unsaturated heterocycle containing from one to four ring heteroatoms selected from nitrogen, oxygen and sulfur;

said cycloalkyl, aryl or Het being optionally substituted with R[6];

wherein R[6] is H, halo, $C_{1-6}$ alkyl, $C_{3-6}$ cycloalkyl, $C_{1-6}$ alkoxy, $C_{3-6}$ cycloalkoxy, $NO_2$, $N(R^7)_2$, NH—C(O)—

R⁷; or NH—C(O)—NH—R⁷, wherein each R⁷ is independently: H, $C_{1-6}$ alkyl or $C_{3-6}$ cycloalkyl;

or R⁶ is NH—C(O)—OR⁸ wherein R⁸ is $C_{1-6}$ alkyl or $C_{3-6}$ cycloalkyl;

R³ is R⁹O— or R⁹NH—, wherein R⁹ is $C_{1-6}$alkyl or $C_{3-6}$cycloalkyl;

R⁴ is H or from one to three substituents on any available carbon atom at positions 8, 9, 10, 11, 12, 13 or 14, said substituent independently selected from the group consisting of: $C_{1-6}$ alkyl, $C_{1-6}$ haloalkyl, $C_{1-6}$ alkoxy, hydroxy, halo, amino, oxo, thio or $C_{1-6}$ thioalkyl;

or a tautomer thereof;

(b) about 0.1 to 10% by weight of a pharmaceutically acceptable amine or a mixture of pharmaceutically acceptable amines;

(c) one or more pharmaceutically acceptable oils;

(d) optionally one or more pharmaceutically acceptable hydrophilic solvents;

(e) optionally one or more pharmaceutically acceptable polymers; and (f) optionally one or more pharmaceutically acceptable surfactants.

The amount of the active ingredient (formula (I) compound) that may be present in the lipid-based system composition may vary widely or be adjusted widely depending on the intended route of administration, the potency of the particular active ingredient being used, the severity of the hepatitis C viral infection and the required concentration. In a particular embodiment, the compound of formula (I) is present in the lipid-based system in an amount of from about 1% to 50% by weight, preferably from about 5% to 30% by weight, more preferably from about 10% to 20% by weight.

Pharmaceutically acceptable amines useful in this composition include the same amines as described above for the "Co-Solvent" system. The amine is present in an amount of about 0.1 to 10% by weight, more preferably in an amount of from about 0.1% to 7% by weight; even more preferably from about 0.1% to 5% by weight.

Pharmaceutically acceptable oils useful in the composition includes a broad spectrum of water-immiscible materials such as, for example, medium or long chain mono-, di- or triglycerides, vegetable oils such as soybean oil, avocado oil, squalene oil, sesame oil, olive oil, canola oil, corn oil, rapeseed oil, safflower oil, and sunflower oil, fish oils, flavored oils, water insoluble vitamins, fatty acids, and mixtures thereof. More preferred oils include mono-, di- or triglycerides of caprylic fatty acids; mono-, di- or triglycerides of capric fatty acids; oleic acid, and mixtures thereof. Some preferred oils include those commercially available under the trade names: Capmul MCM, Capmul MCM C-8, Capmul MCM C-10, Capmul PG-8, Miglyol 810, Captex 355, Miglyol 812, Captex 200, Myvacet, Myverol 18-92, Maisine, and Arlacel 186. The amount of oil(s) in the composition may vary over a wide range and the optimum amount for a particular composition will depend on the type and amount of other the other ingredients in the composition as can be determined by the skilled pharmaceutical technician. In general, however, the pharmaceutically acceptable oil is present in an amount of from about 1% to 99% by weight, more preferably in an amount of from about 20% to 70% by weight.

In certain circumstances, e.g. for the purpose of increasing solubility, improving dispersability, pharmaceutically acceptable hydrophilic solvents can optionally be used in the composition, which include, for example, propylene glycol, polypropylene glycol, polyethylene glycol (e.g., PEG 400), glycerol, ethanol, dimethyl isosorbide, glycofurol, propylene carbonate, dimethyl acetamide, water, or mixtures thereof; preferably, propylene glycol, polyethylene glycol, ethanol, water, or mixtures thereof. A preferred solvent is a mixture of propylene glycol, ethanol and water. The amount of solvent in the composition may vary over a wide range and the optimum amount for a particular composition will depend on the type and amount of other the other ingredients in the composition as can be easily determined by the skilled worker. In general, however, the solvent(s) are present in an amount of up to about 70% by weight, preferably from about 10% to 30% by weight.

To adjust the viscosity of the formulations or to improve stability, pharmaceutically acceptable polymers can optionally be used in the composition, which include, for example, polyethylene glycols (e.g., PEG 1000, PEG 1500, PEG 3350, PEG 6000 and PEG 8000), polyvinylpyrrolidones (e.g., Kollidon 12 PF, Kollidon 17 PF, Kollidon 25 PF, Kollidon 30 PF, Kollidon 90 PF etc.), polyvinylalcohols, cellulose derivatives (e.g., hydroxypropylmethylcellulose (HPMC), hydroxypropylcellulose (HPC)), polyacrylates, polymethacrylates, sugars (e.g., lactose), polyols, and mixtures thereof. When used in the composition, the pharmaceutically acceptable polymer is preferably be present in an amount up to about 50% by weight, preferably about 1 to 20% by weight.

To facilitate self-emulsification, pharmaceutically acceptable surfactants can optionally be used in the composition, which include, for example, vitamin derivatives such as Vitamin E TPGS (d-alpha tocopheryl polyethylene glycol 1000 succinate), polyoxyl castor oils (e.g., Cremophor EL), polyoxyl hydrogenated castor oils, polysorbates (e.g., Tween 80), peglicol 6-oleate, polyoxyethylene stearates, polyglycolyzed glycerides (e.g., Gelucire 44/14) or poloxamers (e.g., Pluronic F68), sodium lauryl sulfate and mixtures thereof. Preferred surfactants include Vitamin E TPGS, polyoxyl 40 hydrogenated castor oil or polyoxyl 35 castor oil, and mixtures thereof.

When used in the composition, the surfactant is preferably present in an amount of up to about 70% by weight, preferably from about 20% to 50% by weight. This type of lipid-based system of the present invention further incorporating a surfactant is generally referred to herein as "self-emulsifying drug delivery system" or "SEDDS".

A particular embodiment of the SEDDS composition according to the present invention is directed to a pharmaceutical composition, comprising:

(a) about 5% to 30% by weight of a compound of formula (I);

(b) about 0.1% to 7% by weight of a pharmaceutically acceptable amine;

(c) about 1% to 99% by weight of a pharmaceutically acceptable oil;

(d) up to about 70% by weight of a pharmaceutically acceptable hydrophilic solvent;

(e) optionally up to about 50% by weight of a pharmaceutically acceptable polymer; and (f) up to about 70% by weight of a pharmaceutically acceptable surfactant.

A further particular embodiment of the SEDDS composition according to the present invention is directed to a pharmaceutical composition, comprising:

(a) about 10% to 20% by weight of a compound of formula (I);

(b) about 0.1% to 5% by weight of a pharmaceutically acceptable amine;

(c) about 20% to 70% by weight of a pharmaceutically acceptable oil;

(d) about 10% to 30% by weight of a pharmaceutically acceptable hydrophilic solvent;

(e) optionally about 1% to 20% by weight of a pharmaceutically acceptable polymer; and (f) about 20% to 50% by weight of a pharmaceutically acceptable surfactant.

A further particular embodiment of the SEDDS composition according to the present invention is directed to a pharmaceutical composition, comprising:

(a) about 10% to 20% by weight of a compound of formula (I);

(b) about 0.1% to 5% by weight of tris(hydroxymethyl) aminomethane;

(c) about 20% to 70% by weight of a mono- or diglyceride of caprylic fatty acid or a mono- or diglyceride of capric fatty acid, or mixtures thereof;

(d) about 10% to 30% by weight of a mixture of propylene glycol, ethanol and optionally water;

(e) optionally about 1% to 20% by weight of polyethylene glycol or polyvinylpyrrolidone; and (f) about 20% to 50% by weight of d-alpha tocopheryl polyethylene glycol 1000 succinate or polyoxyl 35 castor oil (Cremophor EL).

The Lipid-Based System composition may be prepared in a conventional manner, for example, by a method comprising: mixing together the liquid components, e.g., the pharmaceutically acceptable oil(s), and any surfactant(s) and solvent(s); dissolving the pharmaceutically acceptable amine(s) and polymer(s) in the resulting mixture; optionally heating the mixture obtained if necessary to sufficiently melt one or more of the components of the mixture; adding the compound of formula (I) to the resulting mixture and further mixing until all or substantially all of the compound of formula I is solubilized. This method of preparing the composition constitutes another aspect of the present invention. The resulting solution is then optionally formulated into the desired dosage form, for example, capsules, including hard shell or softgel capsules (e.g., hard or soft gelatin capsules), by known manufacturing technology. The composition may also be in the form of a liquid solution or semi-solid for oral, parenteral, rectal or topical administration. Examples of soft gelatin capsules that can be used include those disclosed in EP 649651 B1 and U.S. Pat. No. 5,985,321.

III. Solid Dosage Forms

The present invention also contemplates and includes various solid dosage forms of the composition of the present invention, such as solid dispersions and granulations.

A. Solid Dispersions

The solid dispersion form of the composition of the present invention comprises:

(a) a compound of formula (I):

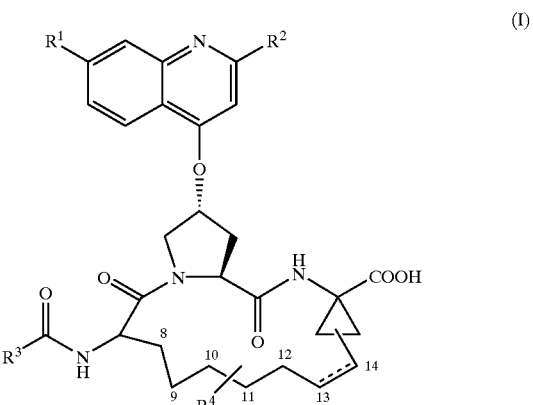

wherein:

—— designates an optional bond forming a double bond between positions 13 and 14;

wherein $R^1$ is H, halo, $C_{1-6}$ alkyl, $C_{3-6}$ cycloalkyl, $C_{1-6}$ haloalkyl, $C_{1-6}$ alkoxy, $C_{3-6}$ cycloalkoxy, hydroxy, or $N(R^5)_2$, wherein each $R^5$ is independently H, $C_{1-6}$ alkyl or $C_{3-6}$ cycloalkyl;

$R^2$ is H, halo, $C_{1-6}$ alkyl, $C_{3-6}$ cycloalkyl, $C_{1-6}$ haloalkyl, $C_6$ thioalkyl, $C_{1-6}$ alkoxy, $C_{3-6}$ cycloalkoxy, $C_{2-7}$ alkoxyalkyl, $C_{6 \text{ or } 10}$ aryl or Het, wherein Het is a five-, six-, or seven-membered saturated or unsaturated heterocycle containing from one to four ring heteroatoms selected from nitrogen, oxygen and sulfur;

said cycloalkyl, aryl or Het being optionally substituted with $R^6$, wherein $R^6$ is H, halo, $C_{1-6}$ alkyl, $C_{3-6}$ cycloalkyl, $C_{1-6}$ alkoxy, $C_{3-6}$ cycloalkoxy, $NO_2$, $N(R^7)_2$, NH—C(O)—$R^7$; or NH—C(O)—NH—$R^7$, wherein each $R^7$ is independently: H, $C_{1-6}$ alkyl or $C_{3-6}$ cycloalkyl;

or $R^6$ is NH—C(O)—$OR^8$ wherein $R^8$ is $C_{1-6}$ alkyl or $C_{3-6}$ cycloalkyl;

$R^3$ is $R^9O$— or $R^9NH$—, wherein $R^9$ is $C_{1-6}$alkyl or $C_{3-6}$cycloalkyl;

$R^4$ is H or from one to three substituents on any available carbon atom at positions 8, 9, 10, 11, 12, 13 or 14, said substituent independently selected from the group consisting of: $C_{1-6}$ alkyl, $C_{1-6}$ haloalkyl, $C_{1-6}$ alkoxy, hydroxy, halo, amino, oxo, thio or $C_{1-6}$ thioalkyl;

or a tautomer thereof;

(b) about 0.1 to 10% by weight of a pharmaceutically acceptable amine or a mixture of pharmaceutically acceptable amines;

(c) one or more pharmaceutically acceptable carriers; and (d) optionally one or more pharmaceutically acceptable surfactants.

The amount of the active ingredient (formula (I) compound) that may be present in the solid dispersion composition may vary widely or be adjusted widely depending on the intended route of administration, the potency of the particular active ingredient being used, the severity of the hepatitis C viral infection and the required concentration. In a particular embodiment, the compound of formula (I) is present in the solid dispersion in an amount of from about 1% to 50% by weight, preferably from about 5% to 30% by weight, more preferably from about 10% to 20% by weight.

Pharmaceutically acceptable amines useful in this composition include, for example, the same amines as described above for the "Co-Solvent" system. The amine is present in an amount of about 0.1 to 10% by weight, more preferably in an amount of from about 0.1% to 7% by weight; even more preferably from about 0.1% to 5% by weight.

Pharmaceutically acceptable carriers that can be used in the composition include any substance that can effectively retain the active ingredient of formula (I) in dispersed state in a final solid dosage form. Suitable pharmaceutically acceptable carriers include, for example, pharmaceutically acceptable polymers and pharmaceutically acceptable ureas. Preferred carriers include polyethylene glycols (e.g., PEG 1000, PEG 1500, PEG 3350, PEG 4600, PEG 6000 and PEG 8000), polyvinylpyrrolidones (e.g., Kollidon 12 PF, Kollidon 17 PF, Kollidon 25 PF, Kollidon 30 PF, Kollidon 90 PF etc.), polyvinylalcohols, cellulose derivatives (e.g., hydroxypropylmethylcellulose (HPMC), hydroxypropylcellulose (HPC)), polyacrylates, polymethacrylates, polyglycolyzed glycerides, ureas, sugars (e.g., lactose), polyols, and mixtures thereof. The best carrier to be used for a particular composition will depend on a variety of factors including the other ingredients in the composition and the specific method to be employed in the preparation of the composition, e.g., co-melting or co-precipitation, as discussed below. For example, when preparing the composition using the co-melt process it is desirable to use a carrier that can be melted under suitable laboratory conditions, for example, at less than about 100° C., preferably less than about 80° C. When preparing the composition using the co-precipitation process it is desirable to use a carrier that can be dissolved in a suitable hydrophilic solvent along with the other ingredients such that co-precipitation can take place.

The amount of pharmaceutically acceptable carrier may vary over a wide range and the optimum amount for a particular composition will again depend on the other ingredients in the composition and the method of preparation to be employed, and can be easily determined by the skilled pharmaceutical technician. In general, however, the pharmaceutically acceptable carrier may be present in the solid dispersion composition in an amount up from about 1 to 99% by weight, preferably about 60% to 80% by weight.

In order to achieve improved dispersion and dissolution performance, pharmaceutically acceptable surfactants can optionally be used in the composition, which include, for example, vitamin derivatives such as Vitamin E TPGS (d-alpha tocopheryl polyethylene glycol 1000 succinate), polyoxyl castor oils (e.g., Cremophor EL), polyoxyl hydrogenated castor oils, polysorbates (e.g., Tween 80), peglicol 6-oleate, polyoxyethylene stearates, polyglycolyzed glycerides such as lauroyl macrogoglycerides (Gelucire 44/14), poloxamers such as polyoxypropylene-polyoxyethylene block copolymer (Pluronic F68), sodium lauryl sulfate (SLS) and mixtures thereof. Preferred surfactants include Vitamin E TPGS, Pluronic F68, or sodium lauryl sulfate, and mixtures thereof. When used in the composition, the surfactant is preferably present in an amount of up to about 50% by weight, preferably from about 1% to 20% by weight.

A particular embodiment of the solid dispersion composition is directed to a pharmaceutical composition comprising:
  (a) about 5% to 30% by weight of a compound of formula (I);
  (b) about 0.1% to 7% by weight of a pharmaceutically acceptable amine;
  (c) about 1% to 99% by weight of a pharmaceutically acceptable carrier; and
  (d) up to about 50% by weight of a pharmaceutically acceptable surfactant.

A further particular embodiment of the solid dispersion composition is directed to a pharmaceutical composition comprising:
  (a) about 10% to 20% by weight of a compound of formula (I);
  (b) about 0.1% to 5% by weight of a pharmaceutically acceptable amine;
  (c) about 60% to 80% by weight of a pharmaceutically acceptable carrier; and
  (d) about 1% to 20% by weight of a pharmaceutically acceptable surfactant.

A further particular embodiment of the solid dispersion composition is directed to a pharmaceutical composition comprising:
  (a) about 10% to 20% by weight of a compound of formula (I);
  (b) about 0.1% to 5% by weight of tris(hydroxymethyl) aminomethane;
  (c) about 60% to 80% by weight of polyethylene glycol, polyvinylpyrrolidone, lactose or a mixture thereof; and
  (d) about 1% to 20% by weight of d-alpha tocopheryl polyethylene glycol 1000 succinate, polyoxypropylene-polyoxyethylene block copolymer, or sodium lauryl sulfate.

The solid dispersion composition may be prepared by two alternative methods: the co-melt method or the co-precipitation method, each of which constitutes another aspect of the present invention.

The co-melt method comprises: (a) mixing the pharmaceutically acceptable carrier(s) and the optional surfactant(s) and heating the resulting mixture to sufficiently melt the carrier(s) and surfactant(s); (b) adding the pharmaceutically acceptable amine(s) and the compound of formula (I) to the mixture obtained in step (a) and mixing until all or substantially all of the compound of formula (I) is solubilized. The resulting dispersion is then allowed to cool and form a solid or semi-solid dispersion. The resulting dispersion is then optionally formulated into the desired dosage form such as, for example, capsules, including hard shell or softgel capsules, by known manufacturing technology. Examples of soft gelatin capsules that can be used include those disclosed in EP 649651 B1 and U.S. Pat. No. 5,985,321.

The co-precipitation method comprises: (a) dissolving the pharmaceutically acceptable amine(s), the pharmaceutically acceptable carrier(s) and optionally the pharmaceutically acceptable surfactant(s) in a suitable hydrophilic solvent; (b) adding the compound of formula (I) to the solution obtained in step (a) and mixing to dissolve the compound of formula (I); and (c) evaporating the hydrophilic solvent to cause co-precipitation of the compound of formula (I), the amine (s), the carrier(s) and the optional surfactant(s). Preferred hydrophilic solvents for use in this process include ethanol, methanol and chloroform. The resulting co-precipitated solid or semi-solid dispersion, generally a powder, is then optionally formulated into the desired dosage form such as, for example, tablets or capsules, including hard shell or softgel capsules, by known manufacturing technology. Examples of soft gelatin capsules that can be used include those disclosed in EP649651 B1 and U.S. Pat. No. 5,985,321.

B. Granulations

The solid dosage form pharmaceutical compositions of the present invention may also be in the form of granulations which are prepared using conventional granulation techniques. Such granulations may generally comprise the same ingredients in the same amounts as is set forth above with respect to the solid dispersion compositions according to the present invention. The resulting granulation is then optionally formulated into the desired dosage form such as, for example, compressed into tablets or filled into capsules, including hard shell capsules, by known manufacturing technology.

The granulations may be prepared by two alternative methods: dry granulation method and wet granulation method, each of which constitutes another aspect of the present invention.

The dry granulation method comprises: (a) triturating and mixing the compound of formula (I), the pharmaceutically acceptable amine(s), the pharmaceutically acceptable carrier(s) and optionally the pharmaceutically acceptable surfactant(s) to form a blend; and (b) optionally adding to the blend a lubricant, e.g. <1% by weight of magnesium stearate. The resulting blended powder may be compressed into tablets.

The wet granulation method comprises: (a) mixing the compound of formula (I), the pharmaceutically acceptable amine(s), the pharmaceutically acceptable carrier(s) and optionally the pharmaceutically acceptable surfactant(s) while adding water or another hydrophilic solvent(s) to the mixture to obtain a paste; (b) drying the paste of step (a) to a sufficient level of dryness; and (c) passing the dried paste through a screen. The resulting granules may be filled into capsules or compressed into tablets.

IV. Optional Additional Ingredients

If desired, the compositions according to the present invention may further include conventional pharmaceutical additives as is necessary or desirable to obtain a suitable formulation, such as antioxidants, lubricants, disintegrants, preservatives, buffers, stabilizers, thickening agents, coloring agents, flavoring agents, fragrances, etc. Additional additives that may be useful in the compositions of the invention are disclosed in Tsantrizos et al.

In one preferred embodiment, the compositions according to the present invention further contain one or more antioxidants. Preferred antioxidants include, for example, ascorbic acid, sulfatide salts, citric acid, propyl gallate, dl-α-tocopherol, ascorbyl palmitate, BHT or BHA. If present, the antioxidant is generally present in an amount of from about 0.01% to 1% by weight.

V. Compounds of Formula (I)

Preferred embodiments for the compounds of formula (I) in the compositions are as set forth below.

Preferred embodiments include compounds of formula I as described above, wherein the cyclopropyl moiety is selected from the 2 different diastereoisomers where the 1-carbon center of the cyclopropyl has the R configuration as represented by structures (i) and (ii):

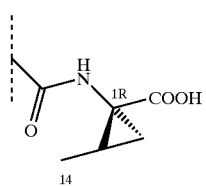 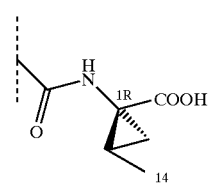

14 syn to the amide (i), or 14 syn to the COOH (ii).

More preferably, position 14 is linked to cyclopropyl group in the configuration syn to the COOH group as represented by structure (ii).

Thus, in one embodiment, in the compound of formula (I) the following moiety:

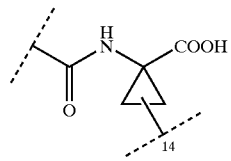

has the configuration represented by the following diastereoisomer:

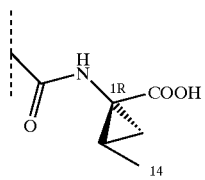

in which configuration position 14 is linked syn to the COOH group.

In another embodiment, in the compound of formula (I):

$R^1$ is H, $C_{1-6}$ alkyl, $C_{1-6}$ alkoxy, hydroxy, chloro, or $N(R^5)_2$, wherein $R^5$ is H or $C_{1-6}$ alkyl; and $R^2$ is H, $C_{1-6}$ thioalkyl, $C_{1-6}$ alkoxy, phenyl or Het selected from the following:

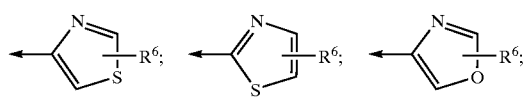

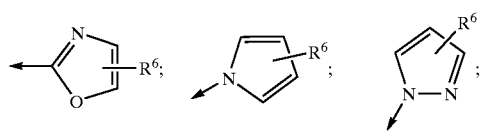

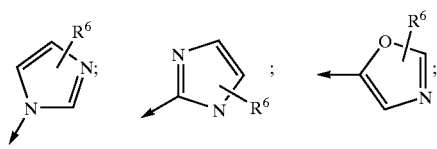

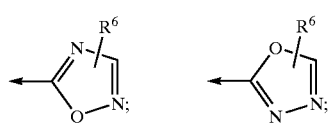

-continued

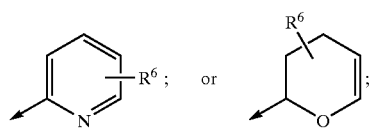

wherein R⁶ is H, $C_{1-6}$ alkyl, NH—R⁷, NH—C(O)—R⁷, NH—C(O)—NH—R⁷, wherein each R⁷ is independently: H, $C_{1-6}$ alkyl, or $C_{3-6}$ cycloalkyl;

or NH—C(O)—OR⁸, wherein R⁸ is $C_{1-6}$ alkyl.

In another embodiment, in the compound of formula (I):

R¹ is H or $C_{1-6}$ alkoxy.

In another embodiment, in the compound of formula (I):

R² is $C_{1-4}$ alkoxy, phenyl or Het selected from the following groups:

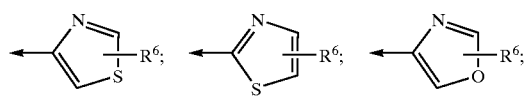

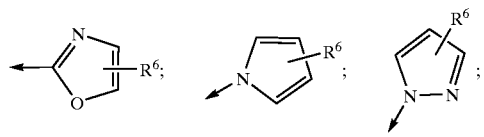

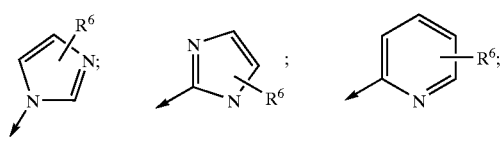

wherein R⁶ is H, $C_{1-6}$ alkyl, NH—R⁷, or NH—C(O)—R⁷;

wherein each R⁷ is H, $C_{1-6}$ alkyl or $C_{3-6}$ cycloalkyl, or NH—C(O)—OR⁸, wherein R⁸ is $C_{1-6}$ alkyl.

In another embodiment, in the compound of formula (I):

R² is ethoxy, or Het selected from the following groups:

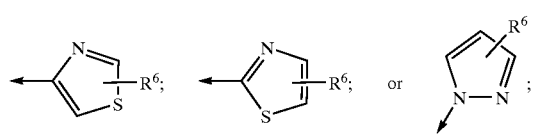

wherein R⁶ is NHR⁷ or NH—C(O)—R⁷, wherein R⁷ is H, $C_{1-6}$ alkyl or $C_{3-6}$ cycloalkyl;

or R⁶ is NH—C(O)—OR⁸, wherein R⁸ is $C_{1-6}$ alkyl.

In another embodiment, in the compound of formula (I):

R² is selected from the following groups:

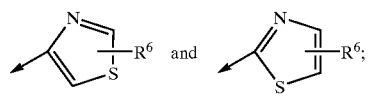

R⁶ is NHR⁷, wherein each R⁷ is independently: H, $C_{1-6}$ alkyl, or $C_{3-6}$ cycloalkyl.

In another embodiment, in the compound of formula (I):

R³ is R⁹O—, wherein R⁹ is butyl, cyclobutyl or cyclopentyl.

In another embodiment, in the compound of formula (I):

the bond at position 13–14 is a single bond.

In another embodiment, in the compound of formula (I):

the bond at position 13–14 is a double bond and said double bond is cis.

In another embodiment, in the compound of formula (I):

R⁴ is H or $C_{1-6}$ alkyl.

In another embodiment, in the compound of formula (I):

R¹ is methoxy;

R² is

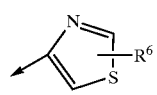

wherein R⁶ is NH—($C_4$alkyl) or NH—($C_{3-6}$cycloalkyl);

R³ is R⁹O—, wherein R⁹ is butyl, cyclobutyl or cyclopentyl;

R⁴ is H or $C_{1-6}$ alkyl;

and following moiety:

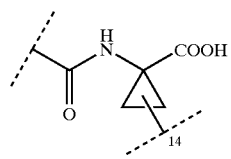

has the configuration represented by the following diastereoisomer:

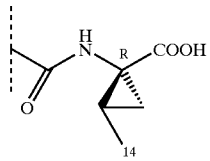

in which configuration position 14 is linked syn to the COOH group.

Tables of Compounds

The following tables list compounds representative of the compounds of formula (I).

TABLE 1

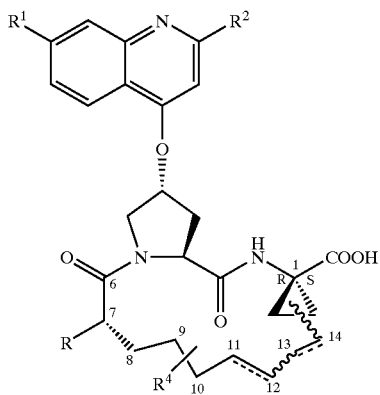

directed to a single stereoisomer at the cyclopropyl moiety, wherein R, $R^4$, said double bond position, cyclopropyl group to 14-position bond stereochemistry, and $R^1$ and $R^2$ are defined as follows:

| Cpd # | R: | $R^4$: | double bond: | cyclopropyl to 14-position bond stereochemistry: | $R^1$: | $R^2$: |
|---|---|---|---|---|---|---|
| 205 | NH-Boc | 11-OH 12-OH cis | none | 1R or 1S, 14 is syn to acid | H | H; |
| 206 | NH-Boc | H | 13,14-cis | 1R, 14 is syn to acid | H | H; |
| 207 | NH-Boc | H | 13,14-cis | 1R, 14 is syn to acid | OMe | H; |
| 208 | NH-Boc | H | 13,14-cis | 1R, 14 is syn to acid | OMe | phenyl; |
| 209 | NH—C(O)—NH-tBu | H | 13,14-cis | 1R, 14 is syn to acid | OMe | phenyl; |
| 210 | NH-Boc | H | 13,14-cis | 1S, 14 is syn to acid | OMe | phenyl; |
| 214 | NH-Boc | 10-oxo | 13,14-cis | 1R, 14 is syn to acid | OMe | phenyl; |
| 215 | NH-Boc | H | none | 1R, 14 is syn to acid | OMe | phenyl; |
| 217 | NH-Boc | 10-OH (mixt dia stereo) | 13,14-cis | 1R, 14 is syn to acid | OMe | phenyl; |
| 218 | NH-Boc | 10-oxo | 13,14-cis | 1R, 14 is syn to amide | OMe | phenyl; |
| And 220 | NH-Boc | H | 13,14-cis | 1R, 14 is syn to amide | OMe | ![thiazole] |

TABLE 2

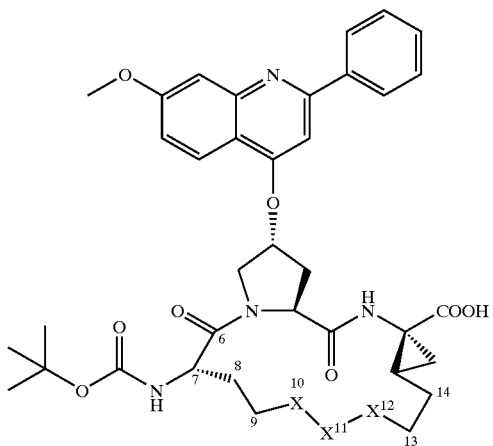

wherein the bond from position 14 to the cyclopropyl group is syn to the COOH, $X_{10}$, $X_{11}$, and $X_{12}$ are defined as follows:

| Cpd # | $X_{10}$: | $X_{11}$: | $X_{12}$: |
|---|---|---|---|
| 502 | $CH_2$ | $CH_2$ | $CH_2$. |

TABLE 3

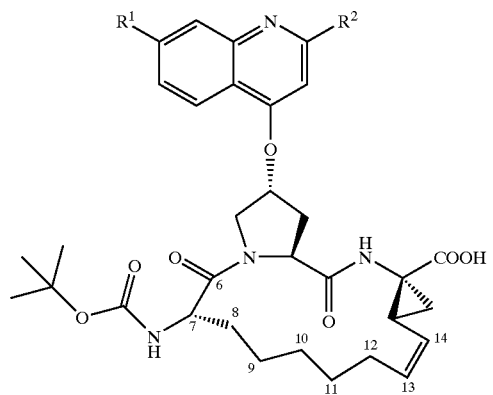

wherein the bond from position 14 to the cyclopropyl group is syn to the COOH, and $R^1$ and $R^2$ are defined as follows:

| Cpd # | $R^1$: | $R^2$: |
|---|---|---|
| 601 | $N(Me)_2$ | ![thiazole-NHAc] |
| 602 | OH | $(CF_3)$; |
| and 603 | OMe | ![oxazole] |

TABLE 4

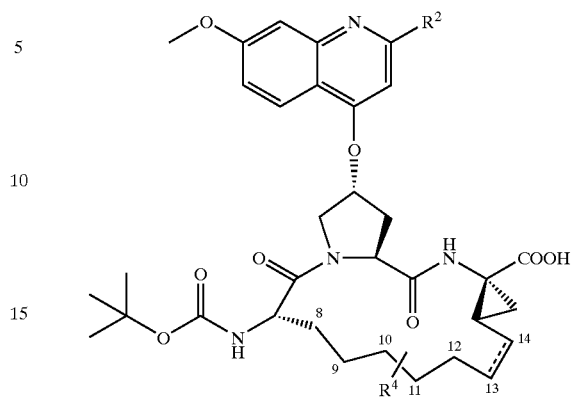

wherein the bond from position 14 to the cyclopropyl group is syn to the COOH, and $R^4$, the 13,14 double bond and $R^2$ are defined as follows:

| Cpd # | $R^4$: | 13,14 double bond: | $R^2$: |
|---|---|---|---|
| 702 | H | Cis |  |
| 703 | H | None | 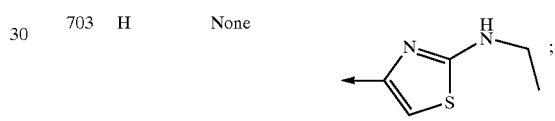 |
| 704 | H | Cis | 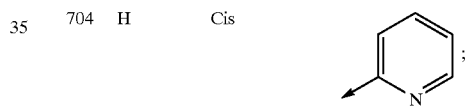 |
| 705 | H | Cis | 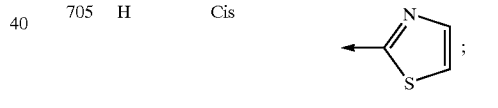 |
| 707 | H | Cis | 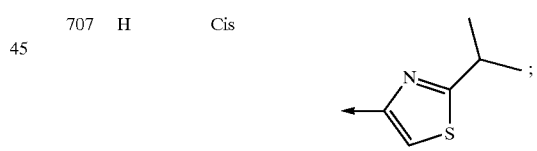 |
| 708 | H | Cis | 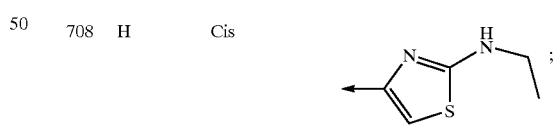 |
| 709 | H | None | 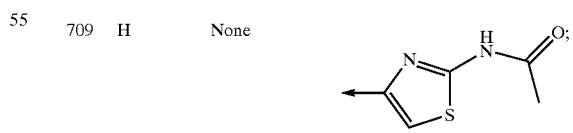 |
| 710 | H | None | 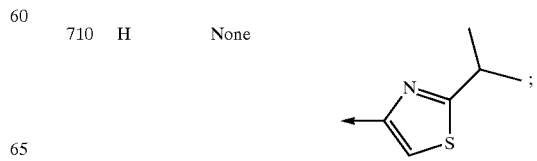 |

TABLE 4-continued

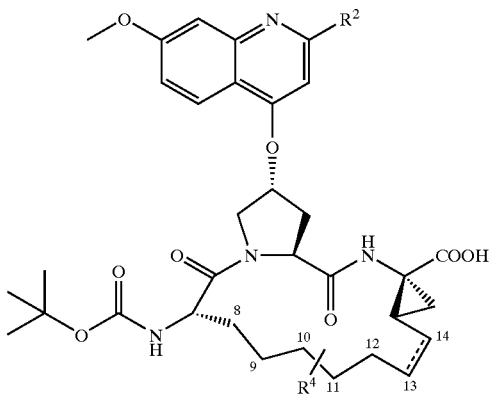

wherein the bond from position 14 to the cyclopropyl group is syn to the COOH, and R⁴, the 13,14 double bond and R² are defined as follows:

| Cpd # | R⁴ | 13,14 double bond | R² |
|---|---|---|---|
| 711 | H | None | (2-pyridyl) |
| 712 | H | Cis | —OEt |
| 713 | H | None | (2-thiazolyl) |
| 714 | H | None | —OEt |
| 715 | H | Cis | (N-pyrrolyl) |
| 716 | H | Cis | (5-methyl-1,3,4-oxadiazol-2-yl) |
| 717 | H | Cis | (3-methyl-1,2,4-oxadiazol-5-yl) |
| 718 | H | Cis | (N-imidazolyl) |
| 719 | H | Cis | (6-methyl-2-pyridyl) |
| 720 | H | None | (2-formamido-thiazol-4-yl) |

TABLE 4-continued

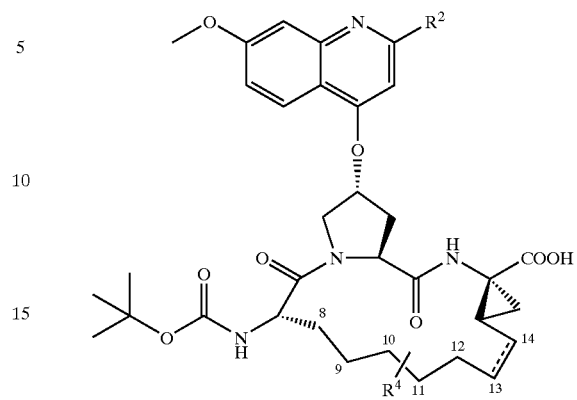

wherein the bond from position 14 to the cyclopropyl group is syn to the COOH, and R⁴, the 13,14 double bond and R² are defined as follows:

| Cpd # | R⁴ | 13,14 double bond | R² |
|---|---|---|---|
| 721 | H | None | (6-methyl-2-pyridyl) |
| 722 | H | Cis | (4-methyl-N-imidazolyl) |
| 723 | H | None | (N-pyrrolyl) |
| 724 | H | None | (2-methoxycarbonylamino-thiazol-4-yl) |
| 725 | H | Cis | (4-isopropyl-thiazol-2-yl) |
| 726 | H | Cis | (1-methyl-imidazol-2-yl) |
| 727 | H | Cis | —CH₂OMe |
| 728 | H | Cis | Me |
| 729 | H | Cis | (2-methylamino-thiazol-4-yl) |

TABLE 4-continued wherein the bond from position 14 to the cyclopropyl group is syn to the COOH, and R⁴, the 13,14 double bond and R² are defined as follows:

| Cpd # | R⁴: | 13,14 double bond: | R²: |
|---|---|---|---|
| 730 | H | None | thiazol-4-yl with 2-NHC(O)NHMe |
| 731 | H | Cis | 2-amino-thiazol-4-yl |
| 732 | H | Cis | 3,4-dihydro-2H-pyran-2-yl |
| 733 | H | Cis | pyrazol-1-yl |
| 734 | H | Cis | 4-methyl-pyrazol-1-yl |
| 735 | H | Cis | 2-(formylamino)-thiazol-4-yl |
| 736 | H | Cis | 2-(methoxycarbonylamino)-thiazol-4-yl |
| 737 | H | Cis | 5-methoxy-pyridin-2-yl |
| 738 | H | Cis | pyrazol-3-yl (N1-linked) |
| 739 | 10-(R) Me | none | Ph |
| 740 | 10-(S) Me | none | Ph |
| and 741 | H | Cis | 2-(isopropylamino)-thiazol-4-yl |

TABLE 5

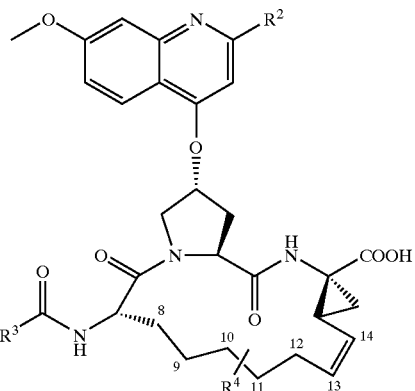

wherein the bond from position 14 to the cyclopropyl group is syn to the COOH, said 13,14 double bond is cis, R³, R⁴ and R² are defined as follows:

| Cpd # | R³: | R⁴: | R²: |
|---|---|---|---|
| 801 | cyclobutyl-O- | H | 2-acetamido-thiazol-4-yl; |
| 804 | (S)-tert-butyl-CH(CH₃)-NH- | H | 2-acetamido-thiazol-4-yl; |
| 805 | cyclopentyl-O- | H | pyrrol-1-yl; |
| 807 | cyclopentyl-O- | H | OEt; |
| 808 | isopropyl-O- | H | OEt; |
| 809 | cyclopentyl-O- | H | 2-acetamido-thiazol-4-yl; |
| 810 | cyclopentyl-O- | H | 2-ethylamino-thiazol-4-yl; |
| 811 | cyclopentyl-O- | H | 2-methylamino-thiazol-4-yl; |
| 812 | cyclopentyl-O- | H | 2-amino-thiazol-4-yl; |

TABLE 5-continued

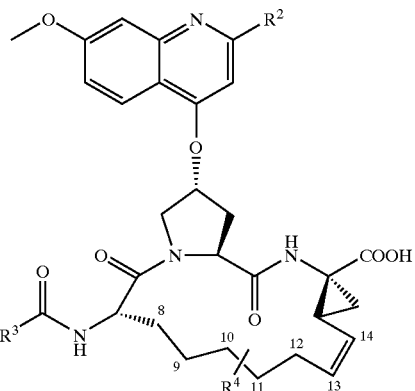

wherein the bond from position 14 to the cyclopropyl group is syn to the COOH, said 13,14 double bond is cis, $R^3$, $R^4$ and $R^2$ are defined as follows:

| Cpd # | $R^3$: | $R^4$: | $R^2$: |
|---|---|---|---|
| 814 | cyclopentyl-O- | H | thiazol-2-yl |
| 815 | cyclopentyl-O- | H | pyridin-2-yl |
| 816 | (S)-3,3-dimethylbutan-2-yl-NH- | H | 2-(methylamino)thiazol-4-yl |
| 817 | cyclopentyl-O- | H | 2-isopropylthiazol-4-yl |
| 818 | cyclopentyl-O- | H | 2-(methoxycarbonylamino)thiazol-4-yl |
| 819 | cyclopentyl-O- | H | 2-(isobutoxycarbonylamino)thiazol-4-yl |
| 820 | cyclobutyl-O- | H | 2-(ethylamino)thiazol-4-yl |
| 821 | cyclopentyl-O- | H | pyrazol-1-yl |

TABLE 5-continued

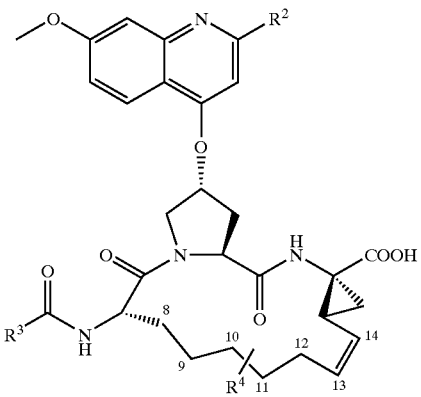

wherein the bond from position 14 to the cyclopropyl group is syn to the COOH, said 13,14 double bond is cis, $R^3$, $R^4$ and $R^2$ are defined as follows:

| Cpd # | $R^3$: | $R^4$: | $R^2$: |
|---|---|---|---|
| 822 | cyclopentyl-O- | H | thiazol-NH-isopropyl |
| 823 | cyclopentyl-O- | H | pyrazolyl |
| 824 | cyclopentyl-O- | 10-(R)Me | OEt; |
| 825 | cyclopentyl-O- | H | thiazol-NH-cyclopropyl |
| 826 | cyclopentyl-O- | H | thiazol-NH-cyclobutyl |
| 827 | cyclopentyl-O- | H | thiazol-NH-cyclopentyl |
| and 828 | cyclopentyl-O- | H | thiazol-NH-cyclohexyl. |

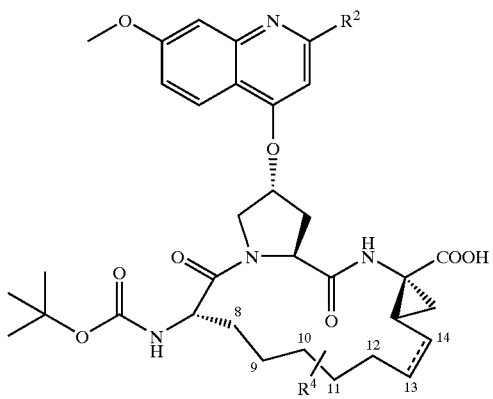

TABLE 6

Additional specific compounds that are representative of the compounds of the present invention may be found in Tsantrizos et al., and such disclosure is herein incorporated by reference.

The compounds of formula I may be synthesized by the procedures fully set forth in Tsantrizos et al, which disclosure is also herein incorporated by reference.

Methods of Therapeutic Use

The compounds of formula I are effective as HCV protease inhibitors, and these compounds and pharmaceutical compositions comprising these compounds are therefore useful in inhibiting the replication of HCV and in the treatment of HCV infections, as fully set forth in Tsantrizos et al., which disclosure is herein incorporated by reference.

As discussed above, the pharmaceutical compositions of the present invention may be formulated into a variety of dosage forms depending upon the particular composition contemplated. Likewise, a variety of modes of administration are possible depending upon the particular composition and dosage form, although oral administration by tablet, capsule or suspension are the preferred modes of administration.

Dosage levels of the compounds of formula (I) and various treatment regimens in the monotherapy for the prevention and treatment of HCV infection are as set forth in Tsantrizos et al. As the skilled artisan will appreciate, however, lower dosages may be possible with the compositions of the present invention depending on the level of improvement in bioavailability. Combination therapy is also possible with one or more additional therapeutic or prophylactic agents as fully described by Tsantrizos et al. The additional agent(s) may be combined with the compounds of this invention to create a single dosage form or, alternatively, these additional agent(s) may be separately administered to a mammal as part of a multiple dosage form.

In order that this invention be more fully understood, the following examples of are set forth. These examples are for the purpose of illustrating embodiments of this invention, and are not to be construed as limiting the scope of the invention in any way.

EXAMPLES

Formulation #1 (Co-Solvent System)

| Ingredient | Weight (mg/g) | % (w/w) |
| --- | --- | --- |
| Compound #822 | 40 | 4 |
| Tromethamine | 32 | 3.2 |
| Water | 448 | 44.8 |
| Ethanol | 213 | 21.3 |
| Propylene glycol | 267 | 26.7 |

Formulation #2 (Co-Solvent System)

| Ingredient | Weight (mg/g) | % (w/w) |
| --- | --- | --- |
| Compound #822 | 100 | 10 |
| Tromethamine | 30 | 3 |
| Water | 420 | 42 |
| Ethanol | 200 | 20 |
| Propylene glycol | 250 | 25 |

Preparation of Formulations 1 and 2

First, Tromethamine was dissolved in a mixture of water, ethanol and propylene glycol in a tightly capped container, and then Compound #822 was added to the solution and stirring was continued until all the drug became soluble.

Formulation #3 (SEDDS)

| Ingredient | Weight (mg/g) | % (w/w) |
| --- | --- | --- |
| Compound #822 | 40 | 4 |
| Tromethamine | 8 | 0.8 |
| Ethanol | 94.7 | 9.47 |
| Propylene glycol | 111.5 | 11.15 |
| Water | 16 | 1.6 |
| Propyl gallate | 2 | 0.2 |
| Capmul MCM | 334.4 | 33.44 |
| Cremophor EL | 393.4 | 39.34 |

Formulation #4 (SEDDS)

| Ingredient | Weight (mg/g) | % (w/w) |
| --- | --- | --- |
| Compound #822 | 125 | 12.5 |
| Tromethamine | 20 | 2 |
| Ethanol | 50 | 5 |
| Propylene glycol | 50 | 5 |
| Water | 20 | 2 |
| Propyl gallate | 2 | 0.2 |
| PEG 3350 | 75 | 7.5 |
| Capmul MCM | 329 | 32.9 |
| $V_E$ TPGS | 329 | 32.9 |

Formulation #5 (Lipid-Based System)

| Ingredient | Weight (mg/g) | % (w/w) |
| --- | --- | --- |
| Compound #822 | 100 | 10 |
| Tromethamine | 4 | 0.4 |
| Ethanol | 100 | 10 |
| Alpha-Tocopherol | 2 | 0.2 |
| Kollidon 12PF | 50 | 5 |
| Capmul MCM | 744 | 74.4 |

Formulation #6 (SEDDS)

| Ingredient | Weight (mg/g) | % (w/w) |
| --- | --- | --- |
| Compound #822 | 100 | 10 |
| Tromethamine | 4 | 0.4 |
| Ethanol | 100 | 10 |
| Propylene glycol | 50 | 5 |
| Alpha-Tocopherol | 2 | 0.2 |
| Kollidon 12PF | 50 | 5 |
| Capmul MCM | 347 | 34.7 |
| $V_E$ TPGS | 347 | 34.7 |

Formulation #6A (SEDDS)

| Ingredient | Weight (mg/g) | % (w/w) |
| --- | --- | --- |
| Compound #822 | 100 | 10 |
| Tromethamine | 10 | 1.0 |
| Water | 20 | 2.0 |
| Ethanol | 100 | 10 |
| Propylene glycol | 50 | 5 |
| Alpha-Tocopherol | 4 | 0.4 |
| Capmul MCM | 220 | 22.0 |
| $V_E$ TPGS | 516 | 49.6 |

Preparation of Formulations 3, 4, 5, 6, and 6A

First, the liquid components such as Capmul MCM, Cremophor EL, propylene glycol, water and ethanol were mixed together in a tightly capped container, and then Tromethamine and antioxidant were dissolved in the mixture. Finally, Compound #822 was added to the container and stirring was continued until the drug was completely solubilized. When $V_E$ TPGS was in the formulation, the mixture was heated at 40° C. in a water bath to melt it before the drug was added. These formulations can be filled into hard shell or soft gelatin capsules.

Formulation #7 (Solid Dispersion—Co-Melt)

| Ingredient | Weight (mg/g) | % (w/w) |
|---|---|---|
| Compound #822 | 125 | 12.5 |
| Tromethamine | 20 | 2 |
| PEG1000 | 755 | 75.5 |
| $V_E$ TPGS | 100 | 10 |

Formulation #8 (Solid Dispersion—Co-Melt)

| Ingredient | Weight (mg/g) | % (w/w) |
|---|---|---|
| Compound #822 | 100 | 10 |
| Tromethamine | 30 | 3 |
| PEG1450 | 770 | 77 |
| $V_E$ TPGS | 100 | 10 |

Preparation of Formulations 7 and 8

PEG and $V_E$ TPGS were placed in a tightly capped container and melted at 60° C. in a water bath. Then, Tromethamine and Compound #822 were added to the container and stirring was continued at the same temperature until the drug was completely solubilized. These formulations can be filled into hard shell or soft gelatin capsules.

Formulation #9 (Solid Dispersion—Co-Precipitate—Comparison Formulation)

| Ingredient | Weight (mg/g) | % (w/w) |
|---|---|---|
| Compound #822 | 200 | 20 |
| Kollidon 25 | 800 | 80 |

Formulation #10 (Solid Dispersion—Co-Precipitate—Invention Formulation)

| Ingredient | Weight (mg/g) | % (w/w) |
|---|---|---|
| Compound #822 | 300 | 30 |
| Kollidon 25 | 670 | 67 |
| Tween 80 | 20 | 2 |
| Tromethamine | 10 | 1 |

Preparation of Formulations 9 and 10

Kollidon 25 and other excipients (e.g., Tween 80 and tromethamine) were dissolved in a sufficient amount of ethanol in a glass container. Then Compound #822 was added to the container and stirred until the compound was completely dissolved. The ethanol was removed by placing the container in a vacuum oven at RT. After the ethanol was completely evaporated, the solid material (co-precipitate) was taken out from the glass container and passed through a 1-mm screen. The powder can be filled into hard shell capsules or further compressed into tablets. The solvent used to dissolve the drug and the excipients can be ethanol, methanol, or chloroform.

Formulation #1 (Dry Granulation)

| Ingredient | Weight (mg/g) | % (w/w) |
|---|---|---|
| Compound #822 | 225 | 22.5 |
| Lactose | 675 | 67.5 |
| Tromethamine | 67.5 | 6.75 |
| SLS | 22.5 | 2.25 |
| Mg Stearate | 10 | 1.0 |

Formulation #12 (Dry Granulation)

| Ingredient | Weight (mg/g) | % (w/w) |
|---|---|---|
| Compound #822 | 225 | 22.5 |
| PEG 4600 | 675 | 67.5 |
| Tromethamine | 67.5 | 6.75 |
| SLS | 22.5 | 2.25 |
| Mg Stearate | 10 | 1.0 |

Preparation of Formulations #11 and #12

In a glass mortar, the formulation ingredients were triturated for about 2 minutes with a glass pestle. The mixture was transferred into a glass bottle and blended with a torbola blender for 6 minutes. The magnesium stearate was added to the powder and blending was continued for another 4 minutes. The powder can be compressed into tablets @ 6.6KN using a 11 mm die set.

Formulation #13 (Wet Granulation)

| Ingredient | Weight (mg/g) | % (w/w) |
|---|---|---|
| Compound #822 | 238 | 23.8 |
| Lactose | 714 | 71.4 |
| PVP (5%) | 48 | 4.8 |

Formulation #14 (Wet Granulation)

| Ingredient | Weight (mg/g) | % (w/w) |
|---|---|---|
| Compound #822 | 230 | 23 |
| Lactose | 688 | 68.8 |
| Tromethamine | 34 | 3.4 |
| PVP (5%) | 48 | 4.8 |

Formulation #15 (Wet Granulation)

| Ingredient | Weight (mg/g) | % (w/w) |
|---|---|---|
| Compound #822 | 216 | 21.6 |
| PEG 4600 | 649 | 64.9 |
| Tromethamine | 65 | 6.5 |
| SLS | 22 | 2.2 |
| PVP (5%) | 48 | 4.8 |

Preparation of Formulations #13, 14 and 15

In a glass mortar, the formulation ingredients were triturated for about 2 minutes with the glass pestle. Hot water (80° C.) was added dropwise to the mixture while stirring with the pestle. Water addition was continued until a paste was obtained. The paste was dried in a petridish in an oven at 45° C. After 2 hours drying, the paste was triturated and passed through a mesh #18. The powder was dried until the weight was constant and equal to the initial weight. The powder can be filled into hard shell capsules or compressed into tablets.

In-Vitro Dispersion and Dissolution Studies (1) Dispersion Test

To assess the dispersability, each prepared formulation was diluted with pH 2.0 (0.05M HCl/KCl) and pH 6.8 buffer (0.05M $KH_2PO_4/K_2HPO$), the dispersion was observed as clear solution, colloidal dispersion (emulsion or microemulsion) or suspension with drug precipitation. Formulations with no drug precipitation in the buffers and faster dispersion rate are preferred.

(2) Dissolution Test

USP XXIII apparatus (paddle method, 50 rpm) was used to obtain the release of drug from selected formulations into 900 ml pH 2.0 buffer (0.05M HCl/KCl) dissolution medium at 37° C. Samples of 10 ml were withdrawn at various time intervals and drug concentration was determined by HPLC. Formulations with faster and higher drug release are preferred.

FIG. 1 shows the in vitro dissolution profiles of four Compound #822 formulations: A conventional suspension containing 1% CMC/0.2% Tween 80 (without tromethamine); Formulation #4 (SEDDS) according to the present invention; Formulation #6A (SEDDS) according to the present invention; and Formulation #7 (Solid Dispersion) according to the present invention. The dissolution test was conducted under the conditions as described above. It can be seen that the compositions of the present invention exhibit superior in vitro dissolution as compared to the conventional suspension.

Figure 2:
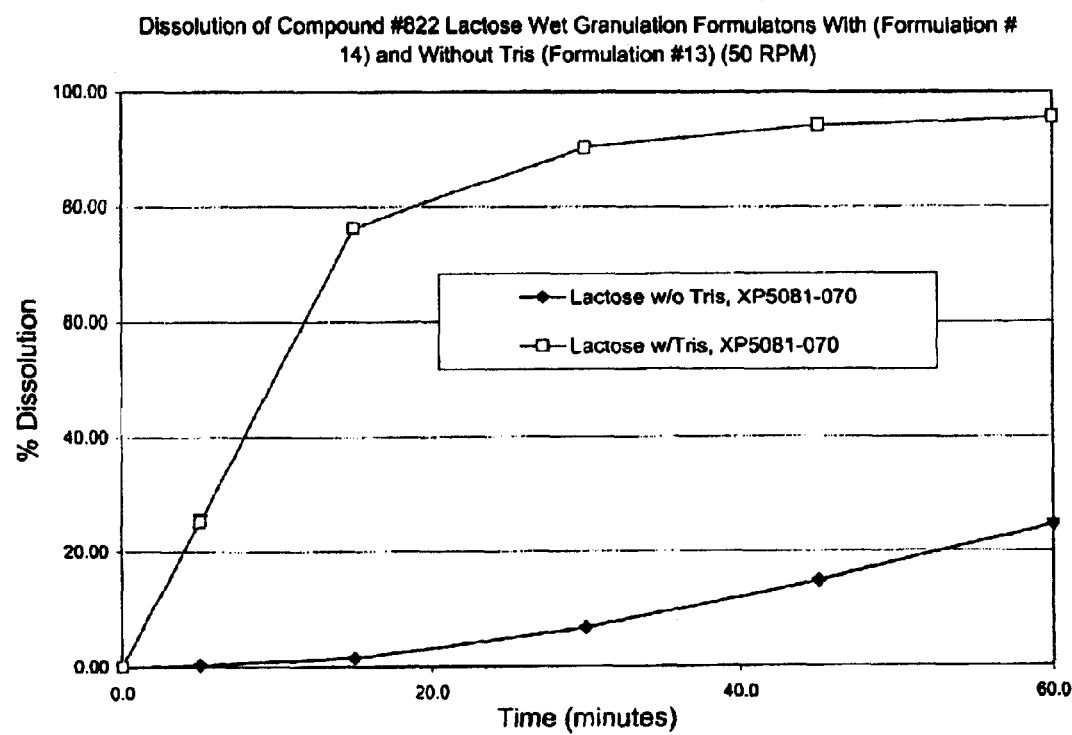
FIG. 2 shows the in-vitro dissolution profiles of a wet granulation formulation according to the present invention containing tromethamine and a comparative formulation without tromethamine.

It has been found that incorporation of a basic amine in a solid dosage form improves the in vitro dissolution rate significantly. Compound #822 is a poorly water soluble compound. Its oral absorption and bioavailability is limited by its dissolution from a solid dosage form. FIG. 2 shows the in vitro dissolution profiles of the wet granulation formulations of Compound #822 with and without tromethamine (Tris), i.e., Formulations #14 and #13, respectively. The dissolution test was conducted under the conditions as described above, except that water containing 0.2% sodium lauryl sulfate (SLS) was used as the dissolution medium.

In-Vivo Bioavailability Studies (1) Bioavailability Study in Rhesus Monkeys

The bioavailability of two formulations (Formulation #1 and Formulation #3) was compared to that of an aqueous suspension containing 0.5% CMC and 0.2% Tween 80 in rhesus monkeys. Two female rhesus monkeys were used in a crossover design with a 2 week washout period between formulations. Monkeys were dosed orally at 40 mg/kg. The PK parameters were summarized in Table 1. The bioavailability for the Formulations #1 and #3 were 15 and 20-fold greater, respectively than that of the CMC/Tween suspension.

TABLE 1

PK parameters of Compound #822 in female rhesus monkeys after a single 40 mg/kg oral dose

| Formulation | Tmax (h) | C max (ng/ml) | AUC (ng. h/ml) | Bioavailability Increase |
|---|---|---|---|---|
| CMC/Tween suspension | 2.0 | 35 ± 1 | 371 ± 6 | 1 |
| Formulation #1 (co-solvent) | 2.0 | 1269 ± 604 | 6026 ± 2350 | 15 |

TABLE 1-continued

PK parameters of Compound #822 in female rhesus monkeys after a single 40 mg/kg oral dose

| Formulation | Tmax (h) | C max (ng/ml) | AUC (ng. h/ml) | Bioavailability Increase |
|---|---|---|---|---|
| Form #3 (SEDDS) | 2.0 | 1595 ± 565 | 8053 ± 3531 | 20 |

(2) Bioavailability Study in Beagle Dogs

The bioavailability of two SEDDS formulations (Formulation #4 and Formulation #6A) and one solid dispersion (Formulation #7) were compared in beagle dogs. The formulations were prepared according to the procedures mentioned above and filled into hard gelatin capsules.

Four dogs (1 male and 3 female) weighing between 10.4 and 14.8 kg were used for the cross-over study. Each dog received a single capsule containing 100 mg Compound #822. Blood samples were taken at 0, 30 min, 1, 1.5, 2, 3, 4, 6, 8, 24 hours after dosing and plasma concentration was analyzed using a LC/MS/MS system. The PK parameters were shown in Table 2. The solid dispersion provided comparable bioavailability as the SEDDS formulations.

TABLE 2

PK parameters (mean + SD) for two oral formulations of Compound #822 in beagle dogs (mg/kg normalized dose)

| Formulation | Tmax (h) | C max (ng/ml) | AUC (ng. h/ml) |
|---|---|---|---|
| Form #4 (SEDDS) | 1.9 ± 1.0 | 1996 ± 676 | 10468 ± 4770 |
| Form #6A (SEDDS) | 2.1 ± 1.2 | 3142 ± 1321 | 14399 ± 6880 |
| Formulation #7 (solid dispersion) | 2.3 ± 1.3 | 1847 ± 621 | 9474 ± 2228 |

We claim:

1. A pharmaceutical composition comprising:

(a) a compound of formula (I):

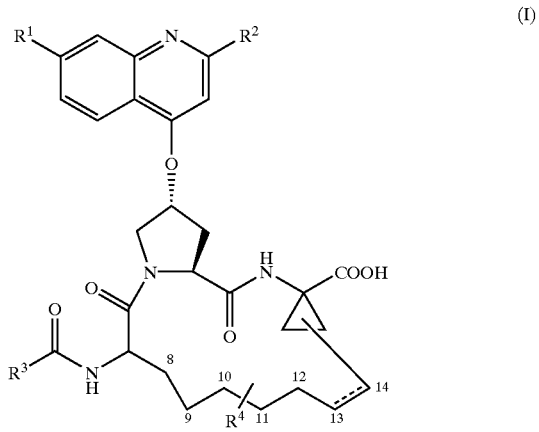

wherein:
- —— designates an optional bond forming a double bond between positions 13 and 14;
- $R^1$ is H, halo, $C_{1-6}$ alkyl, $C_{3-6}$ cycloalkyl, $C_{1-6}$ haloalkyl, $C_{1-6}$ alkoxy, $C_{3-6}$ cycloalkoxy, hydroxy, or $N(R^5)_2$, wherein each $R^5$ is independently H, $C_{1-6}$ alkyl or $C_{3-6}$ cycloalkyl;
- $R^2$ is H, halo, $C_{1-6}$ alkyl, $C_{3-6}$ cycloalkyl, $C_{1-6}$ haloalkyl, $C_{1-6}$ thioalkyl, $C_{1-6}$ alkoxy, $C_{3-6}$ cycloalkoxy, $C_{2-7}$ alkoxyalkyl, $C_{6\ or\ 10}$ aryl or Het, wherein Het is a five-, six-, or seven-membered saturated or unsaturated heterocycle containing from one to four ring heteroatoms selected from nitrogen, oxygen and sulfur;
- said cycloalkyl, aryl or Het being optionally substituted with $R^6$,
- wherein $R^6$ is H, halo, $C_{1-6}$ alkyl, $C_{3-6}$ cycloalkyl, $C_{1-6}$ alkoxy, $C_{3-6}$ cycloalkoxy, $NO_2$, $N(R^7)_2$, NH—C(O)—$R^7$; or NH—C(O)—NH—$R^7$, wherein each $R^7$ is independently: H, $C_{1-6}$ alkyl or $C_{3-6}$ cycloalkyl;
- or $R^6$ is NH—C(O)—$OR^8$ wherein $R^8$ is $C_{1-6}$ alkyl or $C_{3-6}$ cycloalkyl;
- $R^3$ is $R^9$O— or $R^9$NH—, wherein $R^9$ is $C_{1-6}$alkyl or $C_{3-6}$cycloalkyl;
- $R^4$ is H or from one to three substituents on any available carbon atom at positions 8, 9, 10, 11, 12, 13 or 14, said substituent independently selected from the group consisting of: $C_{1-6}$ alkyl, $C_{1-6}$ haloalkyl, $C_{1-6}$ alkoxy, hydroxy, halo, amino, oxo, thio or $C_{1-6}$ thioalkyl;
- or a tautomer thereof;
  - (b) about 0.1 to 10% by weight of a pharmaceutically acceptable amine or a mixture of pharmaceutically acceptable amines; and
  - (c) one or more pharmaceutically acceptable oils;
  - (d) optionally one or more pharmaceutically acceptable hydrophilic solvents;
  - (e) optionally one or more pharmaceutically acceptable polymers; and
  - (f) optionally one or more pharmaceutically acceptable surfactants.

2. A pharmaceutical composition according to claim 1, wherein the compound of formula (I) is present in an amount of from about 1% to 50% by weight.

3. A pharmaceutical composition according to claim 1, wherein the amine is present in an amount of from about 0.1% to 7% by weight.

4. A pharmaceutical composition according to claim 1, wherein the amine is a $C_{1-6}$ alkylamine, di-($C_{1-6}$ alkyl)-amine or tri-($C_{1-6}$ alkyl)-amine, wherein one or more alkyl groups thereof may be optionally substituted by one or more hydroxy groups, or the amine is $C_{1-6}$ alkylenediamine, a basic amino acid or choline hydroxide, or mixtures thereof.

5. A pharmaceutical composition according to claim 1, wherein the amine is selected from ethanolamine, diethanolamine, triethanolamine, tris(hydroxymethyl)aminomethane, ethylenediamine or dimethylaminoethanol, or mixtures thereof.

6. A pharmaceutical composition according to claim 1, wherein the one or more pharmaceutically acceptable oils are present in an amount of from about 1% to 99% by weight.

7. A pharmaceutical composition according to claim 1, wherein the pharmaceutically acceptable oil is selected from: medium or long chain mono-, di- or triglycerides, water insoluble vitamins, fatty acids and mixtures thereof.

8. A pharmaceutical composition according to claim 1, wherein the pharmaceutically acceptable oil is selected from: mono-, di- or triglycerides of caprylic fatty acids; mono-, di- or triglycerides of capric fatty acids; oleic acid, and mixtures thereof.

9. A pharmaceutical composition according to claim 1, wherein the pharmaceutically acceptable hydrophilic solvent is selected from propylene glycol, polypropylene glycol, polyethylene glycol, glycerol, ethanol, dimethyl isosorbide, glycofurol, propylene carbonate, dimethyl acetamide, water, or mixtures thereof.

10. A pharmaceutical composition according to claim 1, wherein the pharmaceutically acceptable hydrophilic solvent is selected from propylene glycol, polyethylene glycol, ethanol, water, and mixtures thereof.

11. A pharmaceutical composition according to claim 1, wherein the pharmaceutically acceptable polymer is present in an amount of up to about 50% by weight.

12. A pharmaceutical composition according to claim 1, wherein the pharmaceutically acceptable polymer is selected from polyethylene glycols, polyvinylpyrrolidones, polyvinylalcohols, cellulose derivatives, polyacrylates, polymethacrylates, sugars, polyols, and mixtures thereof.

13. A pharmaceutical composition according to claim 1, wherein the pharmaceutically acceptable surfactant is present in an amount of up to about 70% by weight.

14. A pharmaceutical composition according to claim 1, wherein the pharmaceutically acceptable surfactant is selected from d-alpha tocopheryl polyethylene glycol 1000 succinate, polyoxyl castor oils, polyoxyl hydrogenated castor oils, polysorbates, peglicol 6-oleate, polyoxyethylene stearates, polyglycolyzed glycerides or poloxamers, or sodium lauryl sulfate and mixtures thereof.

15. A pharmaceutical composition according to claim 1, wherein the pharmaceutically acceptable surfactant is selected from d-alpha tocopheryl polyethylene glycol 1000 succinate, polyoxyl 40 hydrogenated castor oil, polyoxyl 35 castor oil, polyoxypropylene-polyoxyethylene block copolymer, or sodium lauryl sulfate, and mixtures thereof.

16. A pharmaceutical composition according to claim 1, wherein in the compound of formula (I) the following moiety:

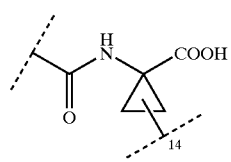

has the configuration represented by the following diastereoisomer:

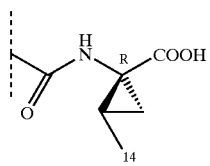

in which configuration position 14 is linked syn to the COOH group.

17. A pharmaceutical composition according to claim 1, wherein in the compound of formula (I):

$R^1$ is H, $C_{1-6}$ alkyl, $C_{1-6}$ alkoxy, hydroxy, chloro, or $N(R^5)_2$, wherein $R^5$ is H or $C_{1-6}$ alkyl; and $R^2$ is H, $C_{1-6}$ thioalkyl, $C_{1-6}$ alkoxy, phenyl or Het selected from the following:

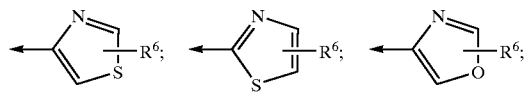

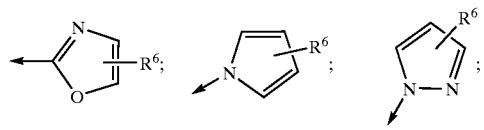

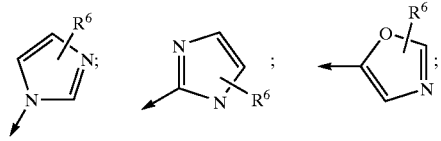

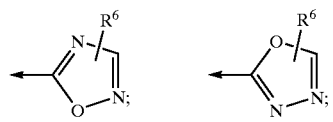

wherein $R^6$ is H, $C_{1-6}$ alkyl, NH—$R^7$, NH—C(O)—$R^7$, NH—C(O)—NH—$R^7$, wherein each $R^7$ is independently: H, $C_{1-6}$ alkyl, or $C_{3-6}$ cycloalkyl;

or NH—C(O)—OR$^8$, wherein $R^8$ is $C_{1-6}$ alkyl.

18. A pharmaceutical composition according to claim 1, wherein $R^2$ is selected from the following groups:

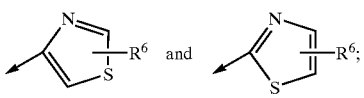

$R^6$ is NHR$^7$, wherein each $R^7$ is independently: H, $C_{1-6}$ alkyl, or $C_{3-6}$ cycloalkyl.

19. A pharmaceutical composition according to claim 1, wherein in the compound of formula (I):

$R^3$ is $R^8$O—, wherein $R^8$ is butyl, cyclobutyl or cyclopentyl.

20. A pharmaceutical composition according to claim 1, wherein in the compound of formula (I) the bond at position 13–14 is a single bond or a double bond and said double bond is cis.

21. A pharmaceutical composition according to claim 1, wherein in the compound of formula (I):

$R^4$ is H or $C_{1-6}$ alkyl.

22. A pharmaceutical composition according to claim 1, wherein in the compound of formula (I):

$R^1$ is methoxy;

$R^2$ is

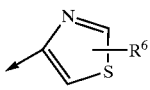

wherein $R^6$ is NH—($C_{1-4}$alkyl) or NH—($C_{3-6}$cycloalkyl);

$R^3$ is $R^9$O—, wherein $R^9$ is butyl, cyclobutyl or cyclopentyl;

$R^4$ is H or $C_{1-6}$ alkyl;

and following moiety:

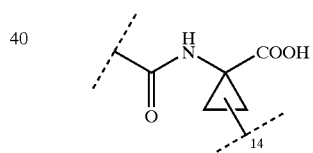

has the configuration represented by the following diastereoisomer:

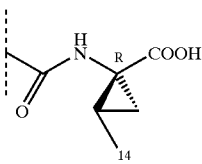

in which configuration position 14 is linked syn to the COOH group.

23. A pharmaceutical composition according to claim 1, wherein the compound of formula (I) is selected from the compounds listed in the following table:

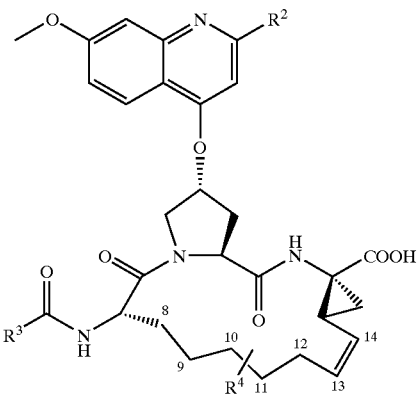

wherein the bond from position 14 to the cyclopropyl group is syn to the COOH, said 13,14 double bond is cis, R³, R⁴ and R² are defined as follows:

| Cpd # | R³: | R⁴: | R²: |
|---|---|---|---|
| 801 | cyclobutyl-O- | H | 2-(acetylamino)thiazol-4-yl |
| 804 | (S)-3,3-dimethyl-2-aminobutyl (N-linked) | H | 2-(acetylamino)thiazol-4-yl |
| 805 | cyclopentyl-O- | H | pyrrol-1-yl |
| 807 | cyclopentyl-O- | H | OEt |
| 808 | isopropyl-O- | H | OEt |
| 809 | cyclopentyl-O- | H | 2-(acetylamino)thiazol-4-yl |
| 810 | cyclopentyl-O- | H | 2-(ethylamino)thiazol-4-yl |
| 811 | cyclopentyl-O- | H | 2-(methylamino)thiazol-4-yl |
| 812 | cyclopentyl-O- | H | 2-aminothiazol-4-yl |
| 814 | cyclopentyl-O- | H | thiazol-2-yl |

-continued
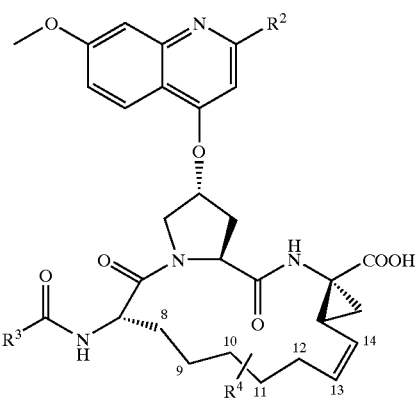
wherein the bond from position 14 to the cyclopropyl group is syn to the COOH, said 13,14 double bond is cis, $R^3$, $R^4$ and $R^2$ are defined as follows:
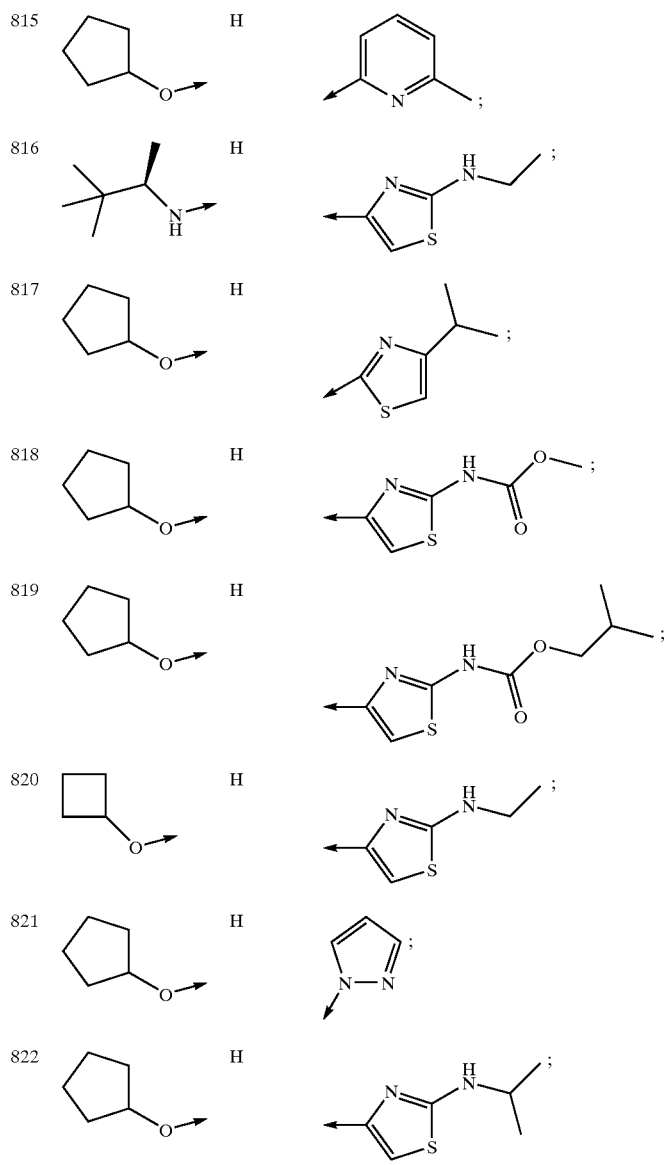

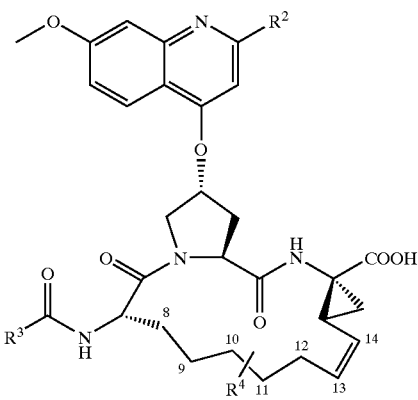

wherein the bond from position 14 to the cyclopropyl group is syn to the COOH, said 13,14 double bond is cis, $R^3$, $R^4$ and $R^2$ are defined as follows:

| Cpd # | $R^3$: | $R^4$: | $R^2$: |
|---|---|---|---|
| 823 | cyclopentyl-O- | H | 4-methyl-pyrazol-1-yl ; |
| 824 | cyclopentyl-O- | 10-(R)Me | OEt; |
| 825 | cyclopentyl-O- | H | 2-(cyclopropylamino)thiazol-4-yl ; |
| 826 | cyclopentyl-O- | H | 2-(cyclobutylamino)thiazol-4-yl ; |
| 827 | cyclopentyl-O- | H | 2-(cyclopentylamino)thiazol-4-yl ; |
| and 828 | cyclopentyl-O- | H | 2-(cyclohexylamino)thiazol-4-yl . |

24. A pharmaceutical composition according to claim 23, wherein the compound of formula (I) is compound 822.

25. A pharmaceutical composition according to claim 1, comprising:
(a) a compound of formula (I);
(b) about 0.1 to 10% by weight of a pharmaceutically acceptable amine or a mixture of pharmaceutically acceptable amines;
(c) one or more pharmaceutically acceptable oils;
(d) optionally one or more pharmaceutically acceptable hydrophilic solvents;
(e) optionally one or more pharmaceutically acceptable polymers; and
(f) optionally one or more pharmaceutically acceptable surfactants.

26. A pharmaceutical composition according to claim 1, comprising:
(a) about 5% to 30% by weight of a compound of formula (I);
(b) about 0.1% to 7% by weight of a pharmaceutically acceptable amine;
(c) about 1% to 99% by weight of a pharmaceutically acceptable oil;
(d) up to about 70% by weight of a pharmaceutically acceptable hydrophilic solvent;
(e) optionally up to about 50% by weight of a pharmaceutically acceptable polymer; and
(f) up to about 70% by weight of a pharmaceutically acceptable surfactant.

27. A pharmaceutical composition according to claim 1, comprising:
(a) about 10% to 20% by weight of a compound of formula (I);
(b) about 0.1% to 5% by weight of a pharmaceutically acceptable amine;
(c) about 20% to 70% by weight of a pharmaceutically acceptable oil;
(d) about 10% to 30% by weight of a pharmaceutically acceptable hydrophilic solvent;
(e) optionally about 1% to 20% by weight of a pharmaceutically acceptable polymer; and
(f) about 20% to 50% by weight of a pharmaceutically acceptable surfactant.

28. A pharmaceutical composition according to claim 1, comprising:
(a) about 10% to 20% by weight of a compound of formula (I);
(b) about 0.1% to 5% by weight of tris(hydroxymethyl) aminomethane;
(c) about 20% to 70% by weight of a mono- or diglyceride of caprylic fatty acid or a mono- or diglyceride of capric fatty acid, or mixtures thereof;
(d) about 10% to 30% by weight of a mixture of propylene glycol, ethanol and optionally water;
(e) optionally about 1% to 20% by weight of polyethylene glycol or polyvinylpyrrolidone; and
(f) about 20% to 50% by weight of d-alpha tocopheryl polyethylene glycol 1000 succinate or polyoxyl 35 castor oil.

29. A pharmaceutical composition according to claim 1, in the form of a fluid dosage form selected from a hard shell or softgel capsule.

30. A pharmaceutical composition according to claim 1, further comprising one or more antioxidants.

31. A pharmaceutical composition according to claim 30, wherein the antioxidant is present in an amount of about 0.01 to 1% by weight.

32. A pharmaceutical composition according to claim 30, wherein the antioxidant is selected from ascorbic acid, sulfatide salts, citric acid, propyl gallate, dl-α-tocopherol, ascorbyl palmitate, BHT or BHA.

33. A method of manufacturing a pharmaceutical composition according to claim 1, said method comprising:
(a) mixing together the pharmaceutically acceptable oil (s), surfactant(s) and solvent(s); (b) dissolving the pharmaceutically acceptable amine(s) in the mixture obtained in step (a); (c) optionally heating the mixture obtained in step (b) if necessary to sufficiently melt one or more of the components of the mixture; (d) adding the compound of formula (I) to the mixture obtained in steps (b) or (c) and mixing.

34. A method of inhibiting the replication of hepatitis C virus by exposing the virus to a hepatitis C viral NS3 protease inhibiting amount of the composition according to claim 1.

35. A method of treating a hepatitis C viral infection in a mammal comprising administering to a mammal in need thereof a therapeutically effective amount of the composition according to claim 1.

36. A pharmaceutical composition comprising:
(a) a compound of formula (I):

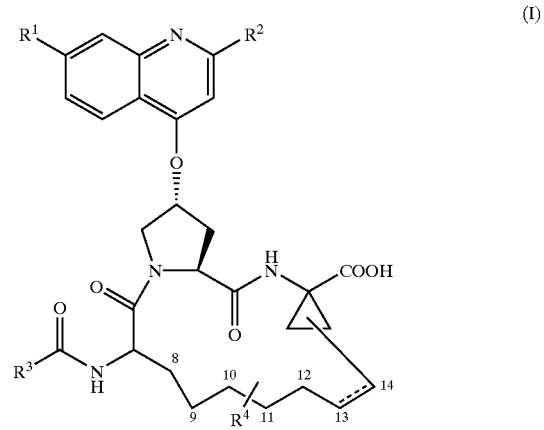

wherein:
—— designates an optional bond forming a double bond between positions 13 and 14;
$R^1$ is H, halo, $C_{1-6}$ alkyl, $C_{3-6}$ cycloalkyl, $C_{1-6}$ haloalkyl, $C_{1-6}$ alkoxy, $C_{3-6}$ cycloalkoxy, hydroxy, or $N(R^5)_2$, wherein each $R^5$ is independently H, $C_{1-6}$ alkyl or $C_{3-6}$ cycloalkyl;
$R^2$ is H, halo, $C_{1-6}$ alkyl, $C_{3-6}$ cycloalkyl, $C_{1-6}$ haloalkyl, $C_{1-6}$ thioalkyl, $C_{1-6}$ alkoxy, $C_{3-6}$ cycloalkoxy, $C_{2-7}$ alkoxyalkyl, $C_{6\ or\ 10}$ aryl or Het, wherein Het is a five-, six-, or seven-membered saturated or unsaturated heterocycle containing from one to four ring heteroatoms selected from nitrogen, oxygen and sulfur;
said cycloalkyl, aryl or Het being optionally substituted with $R^6$,
wherein $R^6$ is H, halo, $C_{1-6}$ alkyl, $C_{3-6}$ cycloalkyl, $C_{1-6}$ alkoxy, $C_{3-6}$ cycloalkoxy, $NO_2$, $N(R^7)_2$, NH—C(O)—$R^7$; or NH—C(O)—NH—$R^7$, wherein each $R^7$ independently: H, $C_{1-6}$ alkyl or $C_{3-6}$ cycloalkyl;
or $R^6$ is NH—C(O)—$OR^8$ wherein $R^8$ is $C_{1-6}$ alkyl or $C_{3-6}$ cycloalkyl;
$R^3$ is $R^9O$— or $R^9NH$—, wherein $R^9$ is $C_{1-6}$alkyl or $C_{3-6}$cycloalkyl;
$R^4$ H or from one to three substituents on any available carbon atom at positions 8, 9, 10, 11, 12, 13 or 14, said substituent independently selected from the group consisting of: $C_{1-6}$ alkyl, $C_{1-6}$ haloalkyl, $C_{1-6}$ alkoxy, hydroxy, halo, amino, oxo, thio or $C_{1-6}$ thioalkyl;
or a tautomer thereof;
(b) about 0.1 to 10% by weight of a pharmaceutically acceptable amine or a mixture of pharmaceutically acceptable amines; and
(c) one or more pharmaceutically acceptable hydrophilic solvents; with the proviso that said pharmaceutical composition does not contain a surfactant.

37. A pharmaceutical composition according to claim 36, wherein the compound of formula (I) is present in an amount of from about 1% to 50% by weight.

38. A pharmaceutical composition according to claim 36, wherein the amine is present in an amount of from about 0.5% to 7% by weight.

39. A pharmaceutical composition according to claim 36, wherein the amine is a $C_{1-6}$ alkylamine, di-($C_{1-6}$ alkyl)-amine or tri-($C_{1-6}$ alkyl)-amine, wherein one or more alkyl groups thereof may be optionally substituted by one or more hydroxy groups, or the amine is $C_{1-6}$ alkylenediamine, a basic amino acid or choline hydroxide, or mixtures thereof.

40. A pharmaceutical composition according to to claim 36, wherein the amine is selected from ethanolamine, diethanolamine, triethanolamine, tris(hydroxymethyl) aminomethane, ethylenediamine or dimethylaminoethanol, or mixtures thereof.

41. A pharmaceutical composition according to to claim 36, wherein the one or more pharmaceutically acceptable hydrophilic solvents are present in an amount of from about 40% to 99% by weight.

42. A pharmaceutical composition according to claim 36, wherein the pharmaceutically acceptable hydrophilic solvent is selected from propylene glycol, polypropylene glycol, polyethylene glycol, glycerol, ethanol, dimethyl isosorbide, glycofurol, propylene carbonate, dimethyl acetamide, water, or mixtures thereof.

43. A pharmaceutical composition according to claim 36, wherein the pharmaceutically acceptable hydrophilic solvent is selected from propylene glycol, polyethylene glycol, ethanol, water, and mixtures thereof.

44. A pharmaceutical composition according to claim 36, wherein in the compound of formula (I):

$R^1$ is methoxy;

$R^2$ is

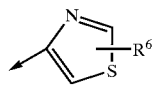

wherein $R^6$ is NH—($C_{1-4}$alkyl) or NH—($C_{3-6}$cycloalkyl);

$R^3$ is $R^9$O—, wherein $R^9$ is butyl, cyclobutyl or cyclopentyl;

$R^4$ is H or $C_{1-6}$ alkyl;

and following moiety:

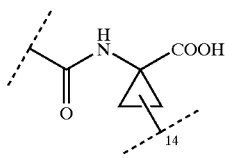

has the configuration represented by the following diastereoisomer:

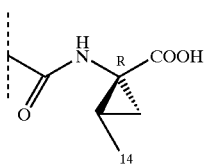

in which configuration position 14 is linked syn to the COOH group.

45. A pharmaceutical composition according to claim 36, wherein the compound of formula (I) is selected from the compounds listed in the following table:

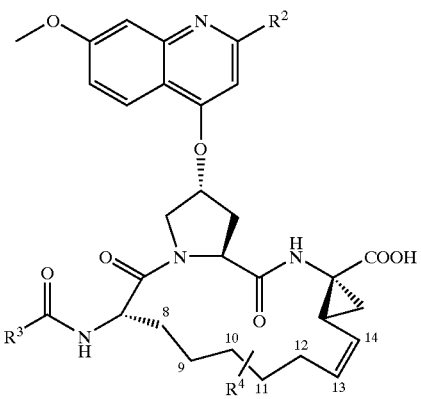

wherein the bond from position 14 to the cyclopropyl group is syn to the COOH, said 13,14 double bond is cis, $R^3$, $R^4$ and $R^2$ are defined as follows:

| Cpd # | $R^3$: | $R^4$: | $R^2$: |
|---|---|---|---|
| 801 | 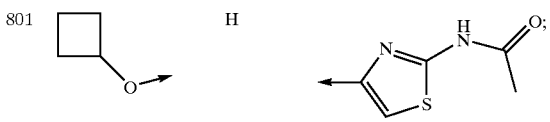 | H | |
| 804 | 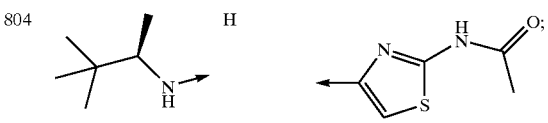 | H | |

-continued

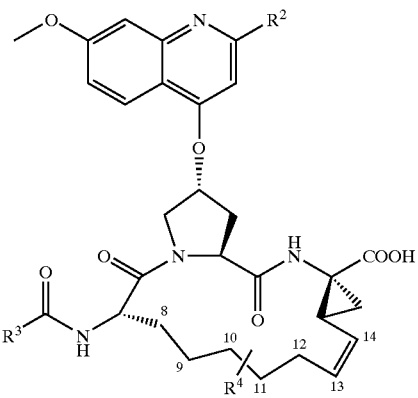

wherein the bond from position 14 to the cyclopropyl group is syn to the COOH, said 13,14 double bond is cis, $R^3$, $R^4$ and $R^2$ are defined as follows:

| Cpd # | $R^3$: | $R^4$: | $R^2$: |
|---|---|---|---|
| 805 | cyclopentyl-O- | H | pyrrolyl |
| 807 | cyclopentyl-O- | H | OEt |
| 808 | isopropyl-O- | H | OEt |
| 809 | cyclopentyl-O- | H | 2-acetamido-thiazol-4-yl |
| 810 | cyclopentyl-O- | H | 2-ethylamino-thiazol-4-yl |
| 811 | cyclopentyl-O- | H | 2-methylamino-thiazol-4-yl |
| 812 | cyclopentyl-O- | H | 2-amino-thiazol-4-yl |
| 814 | cyclopentyl-O- | H | thiazol-2-yl |
| 815 | cyclopentyl-O- | H | 6-methyl-pyridin-2-yl |

-continued
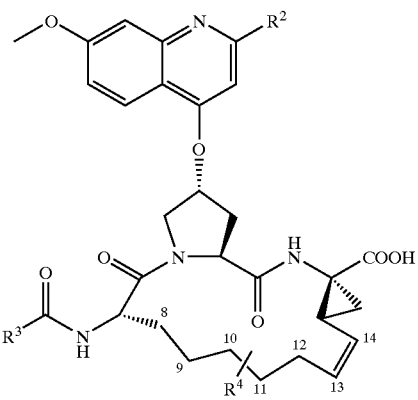
wherein the bond from position 14 to the cyclopropyl group is syn to the COOH, said 13,14 double bond is cis, $R^3$, $R^4$ and $R^2$ are defined as follows:
| Cpd # | $R^3$: | $R^4$: | $R^2$: |
|---|---|---|---|
| 816 | | H | |
| 817 | | H | |
| 818 | | H | |
| 819 | | H | |
| 820 | | H | |
| 821 | | H | |
| 822 | | H | |
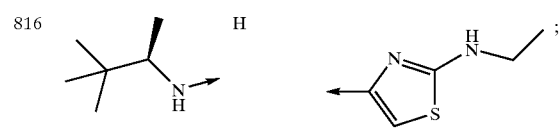
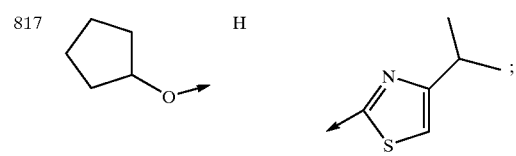
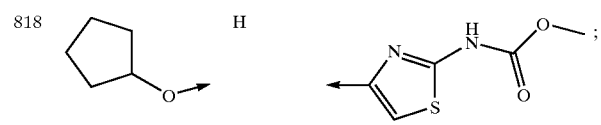
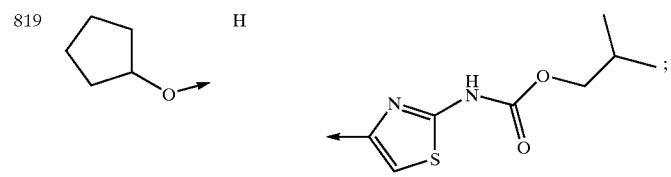
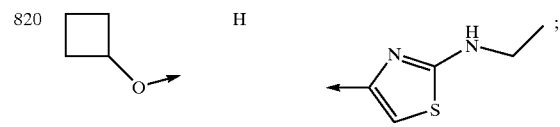
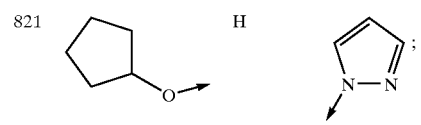
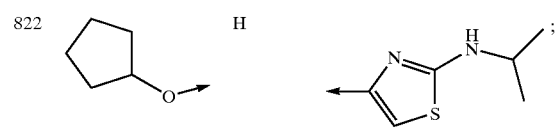

-continued

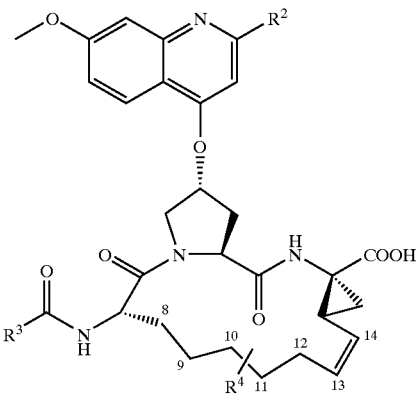

wherein the bond from position 14 to the cyclopropyl group is syn to the COOH, said 13,14 double bond is cis, $R^3$, $R^4$ and $R^2$ are defined as follows:

| Cpd # | $R^3$: | $R^4$: | $R^2$: |
|---|---|---|---|
| 823 | cyclopentyl-O- | H | 4-methylpyrazol-1-yl |
| 824 | cyclopentyl-O- | 10-(R)Me | OEt |
| 825 | cyclopentyl-O- | H | 2-(cyclopropylamino)thiazol-4-yl |
| 826 | cyclopentyl-O- | H | 2-(cyclobutylamino)thiazol-4-yl |
| 827 | cyclopentyl-O- | H | 2-(cyclopentylamino)thiazol-4-yl |
| and 828 | cyclopentyl-O- | H | 2-(cyclohexylamino)thiazol-4-yl |

46. A pharmaceutical composition according to claim 45, wherein the compound of formula (I) is compound 822.

47. A pharmaceutical composition according to claim 36 comprising:
   (a) a compound of formula (I);
   (b) about 0.1 to 10% by weight of a pharmaceutically acceptable amine or a mixture of pharmaceutically acceptable amines; and
   (c) one or more pharmaceutically acceptable hydrophilic solvents.

48. A pharmaceutical composition according to claim 36, comprising:
   (a) about 5% to 30% by weight of a compound of formula (I);
   (b) about 0.5% to 7% by weight of a pharmaceutically acceptable amine; and
   (c) about 40% to 99% by weight of pharmaceutically acceptable hydrophilic solvent.

49. A pharmaceutical composition according to claim 36, comprising:
   (a) about 5% to 15% by weight of a compound of formula (I);
   (b) about 0.5% to 5% by weight of a pharmaceutically acceptable amine; and
   (c) about 80% to 99% by weight of pharmaceutically acceptable hydrophilic solvent.

50. A pharmaceutical composition according to claim 36, comprising:

(a) about 5% to 15% by weight of a compound of formula (I);
(b) about 0.5% to 5% by weight of tris(hydroxymethyl) aminomethane; and
(c) about 80% to 90% by weight of a mixture of propylene glycol, ethanol and water.

51. A pharmaceutical composition according to claim 36, in the form of a topical, parenteral or oral dosage form.

52. A pharmaceutical composition according to claim 36, further comprising one or more antioxidants.

53. A method of manufacturing a pharmaceutical composition according to claim 36, said method comprising: (a) dissolving the amine(s) in the one or more pharmaceutically acceptable solvents; (b) adding the compound of formula (I) to the solution obtained in step (a) and mixing.

54. A method of inhibiting the replication of hepatitis C virus by exposing the virus to a hepatitis C viral NS3 protease inhibiting amount of the composition according to claim 36.

55. A method of treating a hepatitis C viral infection in a mammal comprising administering to a mammal in need thereof a therapeutically effective amount of the composition according to claim 36.

56. A pharmaceutical composition in the form of a solid or semi-solid dispersion or granulation comprising:
(a) a compound of formula (I):

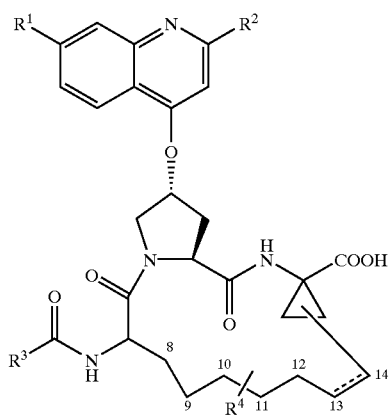

wherein:
——— designates an optional bond forming a double bond between positions 13 and 14;
$R^1$ is H, halo, $C_{1-6}$ alkyl, $C_{3-6}$ cycloalkyl, $C_{1-6}$ haloalkyl, $C_{1-6}$ alkoxy, $C_{3-6}$ cycloalkoxy, hydroxy, or $N(R^5)_2$, wherein each $R^5$ is independently H, $C_{1-6}$ alkyl or $C_{3-6}$ cycloalkyl;
$R^2$ is H, halo, $C_{1-6}$ alkyl, $C_{3-6}$ cycloalkyl, $C_{1-6}$ haloalkyl, $C_{1-6}$ thioalkyl, $C_{1-6}$ alkoxy, $C_{3-6}$ cycloalkoxy, $C_{2-7}$ alkoxyalkyl, $C_{6\ or\ 10}$ aryl or Het, wherein Het is a five-, six-, or seven-membered saturated or unsaturated heterocycle containing from one to four ring heteroatoms selected from nitrogen, oxygen and sulfur;
said cycloalkyl, aryl or Het being optionally substituted with $R^6$,
wherein $R^6$ is H, halo, $C_{1-6}$ alkyl, $C_{3-6}$ cycloalkyl, $C_{1-6}$ alkoxy, $C_{3-6}$ cycloalkoxy, $NO_2$, $N(R^7)_2$, NH—C(O)—$R^7$; or NH—C(O)—NH—$R^7$, wherein each $R^7$ independently: H, $C_{1-6}$ alkyl or $C_{3-6}$ cycloalkyl;
or $R^6$ is NH—C(O)—$OR^8$ wherein $R^8$ is $C_{1-6}$ alkyl or $C_{3-6}$ cycloalkyl;

$R^3$ is $R^9$O— or $R^9$NH—, wherein $R^9$ is $C_{1-6}$ alkyl or $C_{3-6}$ cycloalkyl;
$R^4$ H or from one to three substituents on any available carbon atom at positions 8, 9, 10, 11, 12, 13 or 14, said substituent independently selected from the group consisting of: $C_{1-6}$ alkyl, $C_{1-6}$ haloalkyl, $C_{1-6}$ alkoxy, hydroxy, halo, amino, oxo, thio or $C_{1-6}$ thioalkyl;

or a tautomer thereof;

(b) about 0.1 to 10% by weight of a pharmaceutically acceptable amine or a mixture of pharmaceutically acceptable amines; and
(c) one or more pharmaceutically acceptable carriers; and
(d) optionally one or more pharmaceutically acceptable surfactants.

57. A pharmaceutical composition according to claim 56, wherein the compound of formula (I) is present in an amount of from about 1% to 50% by weight.

58. A pharmaceutical composition according to claim 56, wherein the amine is present in an amount of from about 0.1% to 7% by weight.

59. A pharmaceutical composition according to claim 56, wherein the amine is a $C_{1-6}$ alkylamine, di-($C_{1-6}$ alkyl)-amine or tri-($C_{1-6}$ alkyl)-amine, wherein one or more alkyl groups thereof may be optionally substituted by one or more hydroxy groups, or the amine is $C_{1-6}$ alkylenediamine, a basic amino acid or choline hydroxide, or mixtures thereof.

60. A pharmaceutical composition according to claim 56, wherein the amine is selected from ethanolamine, diethanolamine, triethanolamine, tris(hydroxymethyl) aminomethane, ethylenediamine or dimethylaminoethanol, or mixtures thereof.

61. A pharmaceutical composition according to claim 56, wherein the pharmaceutically acceptable carrier is selected from a pharmaceutically acceptable polymer and a pharmaceutically acceptable urea.

62. A pharmaceutical composition according to claim 56, wherein the pharmaceutically acceptable carrier is selected from polyethylene glycols having a molecular weight from 1000 to 8000, polyvinylpyrrolidones, polyvinylalcohols, cellulose derivatives, polyacrylates, polymethacrylates, polyglycolyzed glycerides, ureas, sugars, polyols, and mixtures thereof.

63. A pharmaceutical composition according to claim 56, wherein the pharmaceutically acceptable surfactant is present in an amount of up to about 50% by weight.

64. A pharmaceutical composition according to claim 56, wherein the pharmaceutically acceptable surfactant is selected from d-alpha tocopheryl polyethylene glycol 1000 succinate, polyoxyl castor oils, polyoxyl hydrogenated castor oils, polysorbates, peglicol 6-oleate, polyoxyethylene stearates, polyglycolyzed glycerides or poloxamers, or sodium lauryl sulfate and mixtures thereof.

65. A pharmaceutical composition according to claim 56, wherein the pharmaceutically acceptable surfactant is selected from d-alpha tocopheryl polyethylene glycol 1000 succinate, polyoxypropylene-polyoxyethylene block copolymer, or sodium lauryl sulfate, and mixtures thereof.

66. A pharmaceutical composition according to claim 56, wherein in the compound of formula (I):

$R^1$ is methoxy;

$R^2$ is

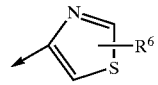

wherein $R^6$ is NH—($C_{1-4}$alkyl) or NH—($C_{3-6}$cycloalkyl);

$R^3$ is $R^9$O—, wherein $R^9$ is butyl, cyclobutyl or cyclopentyl;

$R^4$ is H or $C_{1-6}$ alkyl;

and following moiety:

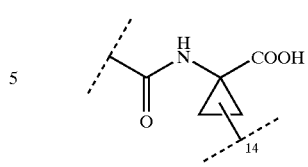

has the configuration represented by the following diastereoisomer:

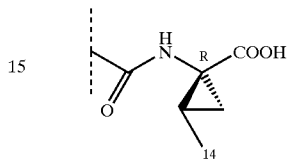

in which configuration position 14 is linked syn to the COOH group.

67. A pharmaceutical composition according to claim 56, wherein the compound of formula (I) is selected from the compounds listed in the following table:

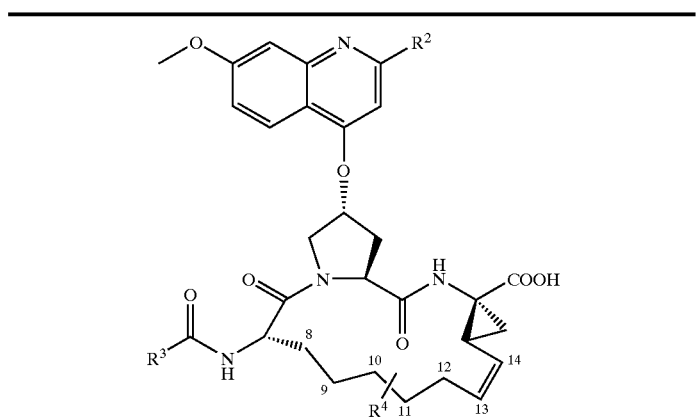

wherein the bond from position 14 to the cyclopropyl group is syn to the COOH, said 13,14 double bond is cis, $R^3$, $R^4$ and $R^2$ are defined as follows:

| Cpd # | $R^3$: | $R^4$: | $R^2$: |
|---|---|---|---|
| 801 | 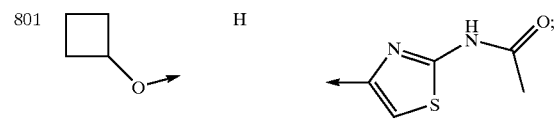 | H | |
| 804 | 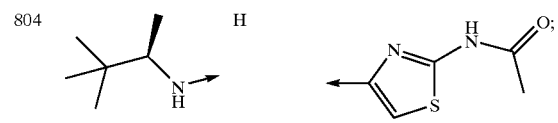 | H | |
| 805 | 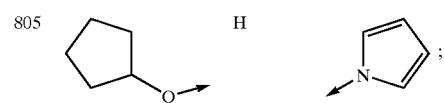 | H | |
| 807 | 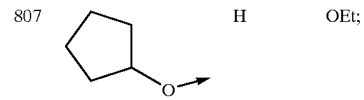 | H | OEt; |

-continued

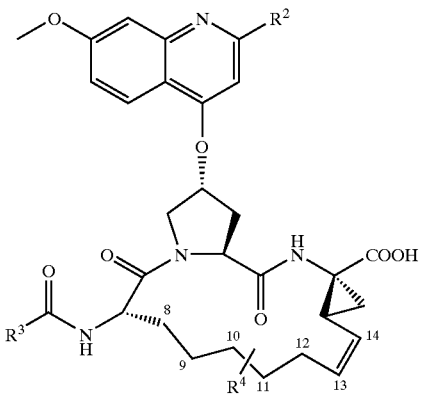

wherein the bond from position 14 to the cyclopropyl group is syn to the COOH, said 13,14 double bond is cis, R³, R⁴ and R² are defined as follows:

| Cpd # | R³: | R⁴: | R²: |
|---|---|---|---|
| 808 | iPrO- | H | OEt; |
| 809 | cyclopentyl-O- | H | thiazol-NHC(O)CH₃; |
| 810 | cyclopentyl-O- | H | thiazol-NHEt; |
| 811 | cyclopentyl-O- | H | thiazol-NHMe; |
| 812 | cyclopentyl-O- | H | thiazol-NH₂; |
| 814 | cyclopentyl-O- | H | thiazol-yl; |
| 815 | cyclopentyl-O- | H | pyridin-2-yl; |
| 816 | tBuCH(Me)NH- | H | thiazol-NHEt; |
| 817 | cyclopentyl-O- | H | 2-methylthiazol-4-yl-iPr; |

-continued

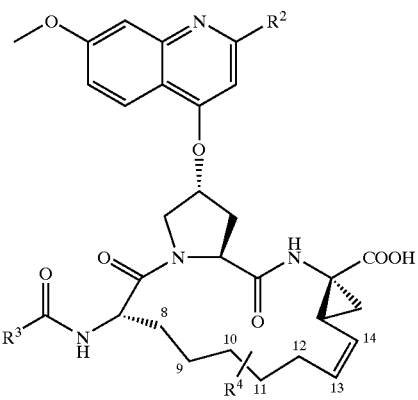

wherein the bond from position 14 to the cyclopropyl group is syn to the COOH, said 13,14 double bond is cis, $R^3$, $R^4$ and $R^2$ are defined as follows:

| Cpd # | $R^3$: | $R^4$: | $R^2$: |
|---|---|---|---|
| 818 | cyclopentyl-O- | H | thiazole-NHC(O)OMe |
| 819 | cyclopentyl-O- | H | thiazole-NHC(O)O-iBu |
| 820 | cyclobutyl-O- | H | thiazole-NHEt |
| 821 | cyclopentyl-O- | H | pyrazole |
| 822 | cyclopentyl-O- | H | thiazole-NH-iPr |
| 823 | cyclopentyl-O- | H | 4-methylpyrazole |
| 824 | cyclopentyl-O- | 10-(R)Me | OEt |
| 825 | cyclopentyl-O- | H | thiazole-NH-cyclopropyl |

-continued

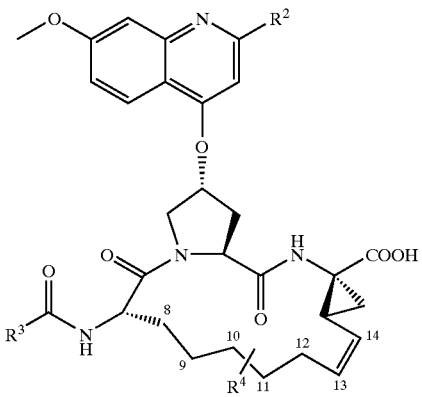

wherein the bond from position 14 to the cyclopropyl group is syn to the COOH, said 13,14 double bond is cis, R³, R⁴ and R² are defined as follows:

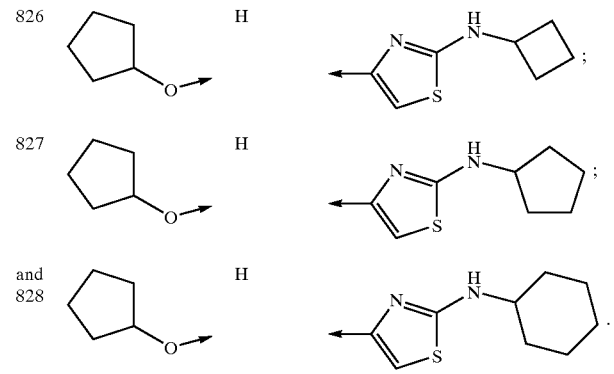

68. A pharmaceutical composition according to claim 67, wherein the compound of formula (I) is compound 822.

69. A pharmaceutical composition according to claim 56, comprising:
(a) a compound of formula (I);
(b) about 0.1 to 10% by weight of a pharmaceutically acceptable amine or a mixture of pharmaceutically acceptable amines;
(c) one or more pharmaceutically acceptable carriers; and
(d) optionally one or more pharmaceutically acceptable surfactants.

70. A pharmaceutical composition according to claim 56, comprising:
(a) about 5% to 30% by weight of a compound of formula (I);
(b) about 0.1% to 7% by weight of a pharmaceutically acceptable amine;
(c) about 1% to 99% by weight of a pharmaceutically acceptable carrier; and
(d) up to about 50% by weight of a pharmaceutically acceptable surfactant.

71. A pharmaceutical composition according to claim 56, comprising:
(a) about 10% to 20% by weight of a compound of formula (I);
(b) about 0.1% to 5% by weight of a pharmaceutically acceptable amine;
(c) about 60% to 80% by weight of a pharmaceutically acceptable carrier; and
(d) about 1% to 20% by weight of a pharmaceutically acceptable surfactant.

72. A pharmaceutical composition according to claim 56, comprising:
(a) about 10% to 20% by weight of a compound of formula (I);
(b) about 0.1% to 5% by weight of tris(hydroxymethyl) aminomethane;
(c) about 60% to 80% by weight of a polyethylene glycol having a molecular weight from 1000 to 8000, polyvinylpyrrolidone, lactose or a mixture thereof; and
(d) about 1% to 20% by weight of d-alpha tocopheryl polyethylene glycol 1000 succinate, polyoxypropylene-polyoxyethylene block copolymer or sodium lauryl sulfate.

73. A pharmaceutical composition according to claim 56, in the form of a solid dosage form selected from a powder, a tablet or a capsule.

74. A pharmaceutical composition according to claim 56, further comprising one or more antioxidants.

75. A method of manufacturing a pharmaceutical composition according to claim 56, said method comprising:
(A) (a) dissolving the pharmaceutically acceptable amine(s), the pharmaceutically acceptable carrier(s) and optionally the pharmaceutically acceptable surfactant(s) in a suitable hydrophilic solvent; (b) adding the compound of formula (I) to the solution obtained in step (a) and mixing to dissolve the compound of formula (I); (c) evaporating the hydrophilic solvent to cause co-precipitation of the compound of formula (I), the amine(s), the carrier(s) and the optional surfactant(s); or (B) (a) mixing the pharmaceutically acceptable carrier(s) and the optional surfactant(s) and heating the resulting mixture to sufficiently melt the carrier(s) and surfactant(s); (b) adding the pharmaceutically acceptable amine(s) and the compound of formula (I) to the mixture obtained in step (a) and mixing; or (C) (a) mixing the compound of formula (I), the pharmaceutically acceptable amine(s), the pharmaceutically acceptable carrier(s) and optionally the pharmaceutically acceptable surfactant(s) to form a blend, and (b) optionally adding a lubricant to the blend; or (D) (a) mixing the compound of formula (I), the pharmaceutically acceptable amine(s), the pharmaceutically acceptable carrier(s) and optionally the pharmaceutically acceptable surfactant(s) while adding water or another hydrophilic solvent(s) to the mixture to obtain a paste; (b) drying the paste of step (a) to a sufficient level of dryness; and (c) passing the dried paste through a screen.

76. A method of inhibiting the replication of hepatitis C virus by exposing the virus to a hepatitis C viral NS3 protease inhibiting amount of the composition according to claim 56.

77. A method of treating a hepatitis C viral infection in a mammal comprising administering to a mammal in need thereof a therapeutically effective amount of the composition according to claim 56.

* * * * *